United States Patent
Betts-Lacroix et al.

(10) Patent No.: US 10,596,198 B1
(45) Date of Patent: Mar. 24, 2020

(54) DEVICES FOR SELECTIVELY RELEASING VOLATILE COMPOUNDS

(71) Applicant: Vium, Inc., San Mateo, CA (US)

(72) Inventors: Jonathan Noble Betts-Lacroix, Belmont, CA (US); Daniel Ford, San Francisco, CA (US); Laura Schaevitz, Los Gatos, CA (US)

(73) Assignee: Vium, Inc., San Mateo, CA (US)

( * ) Notice: Subject to any disclaimer, the term of this patent is extended or adjusted under 35 U.S.C. 154(b) by 0 days.

(21) Appl. No.: 14/871,986

(22) Filed: Sep. 30, 2015

(51) Int. Cl.
| | |
|---|---|
| *A61B 5/00* | (2006.01) |
| *A61K 35/22* | (2015.01) |
| *A61J 3/00* | (2006.01) |
| *A01K 1/03* | (2006.01) |
| *A61K 41/00* | (2020.01) |
| *A61K 9/00* | (2006.01) |

(52) U.S. Cl.
CPC ............. *A61K 35/22* (2013.01); *A01K 1/031* (2013.01); *A61B 5/4011* (2013.01); *A61J 3/00* (2013.01); *A61K 9/0043* (2013.01); *A61K 41/00* (2013.01); *A61J 2200/42* (2013.01)

(58) Field of Classification Search
CPC ................................ A61B 5/4011; A61B 5/00
USPC ........................................................ 422/120
See application file for complete search history.

(56) References Cited

U.S. PATENT DOCUMENTS

| | | | | |
|---|---|---|---|---|
| 3,608,062 A * | 9/1971 | Alfes | ...................... | A01N 25/18 239/6 |
| 4,845,887 A | 7/1989 | Snyder | | |
| 5,139,864 A * | 8/1992 | Lindauer | ................. | A01N 25/18 428/304.4 |
| 6,053,738 A | 4/2000 | Ivey, Jr. | | |
| 6,231,032 B1 | 5/2001 | Ivey, Jr. | | |
| 6,551,560 B1 * | 4/2003 | Flashinski | ........... | A01M 1/2077 219/392 |
| 6,602,475 B1 * | 8/2003 | Chiao | ..................... | A61L 9/035 222/146.5 |
| 7,691,336 B2 * | 4/2010 | Westring | ............. | A01M 1/2033 261/26 |
| 7,718,119 B2 | 5/2010 | Tajima | | |
| 8,747,735 B2 * | 6/2014 | Homer | .................... | B05B 17/04 422/123 |
| 8,765,073 B1 * | 7/2014 | Hsiao | ........................ | A61L 2/00 239/34 |
| 2011/0110824 A1 * | 5/2011 | Hsiao | ..................... | A61L 9/035 422/125 |
| 2012/0000989 A1 | 1/2012 | Bordier | | |
| 2013/0084535 A1 * | 4/2013 | Braun | ..................... | C11C 5/008 431/288 |

(Continued)

OTHER PUBLICATIONS

Chabout et al, Adult Male Mice Emit Context-Specific Ultrasonic Vocalizations . . . , Jan. 6, 2012, PLoS ONE 7(1): e29401.

(Continued)

*Primary Examiner* — Kevin Joyner
(74) *Attorney, Agent, or Firm* — Nienstadt PLLC

(57) ABSTRACT

An apparatus for sequestering and releasing compounds into the air is provided. The apparatus includes a card with a first side and a second side, and a plurality of compound-sequestering structures affixed to the first side. Each of the plurality of compound-sequestering structures is configured to release a compound into the air when heated to a first temperature.

20 Claims, 16 Drawing Sheets

(56) References Cited

U.S. PATENT DOCUMENTS

2015/0174003 A2* 6/2015 O'Keeffe ............... A61H 33/06
4/524

OTHER PUBLICATIONS

Asaba et al., Sexual attractiveness of male chemicals and vocalizations in mice, Aug. 5, 2014, vol. 8, Art. 231, Frontiers in Neurocience.
Tong et al., Properties and mechanisms of olfactory learning and memory, Jul. 7, 2014, vol. 8 Art. 238, Frontiers in Behavioral Neurocience.
Chabout et al., Male mice song syntax depends on social contexts and influences female preferences, Apr. 1, 2015, vol. 9 Art. 76, Frontiers in Behavioral Neurocience.
"Higher Alcanes" Wikipedia p., accessed May 5, 2015, available at https://en.wikipedia.org/w/index.php?title=Higher_alkanes&oldid=660974133.
Yang et al. Simple Behavioral Assessment of Mouse Olfaction, Jul. 2009, Unit-8.24, Curr Protoc Neurosci.
U.S. Appl. No. 14/788,749, filed Jun. 30, 2015, to Heath et al.
U.S. Appl. No. 14/871,966, filed Sep. 30, 2015, to Betts-Lacroix et al.
U.S. Appl. No. 14/549,403, filed Nov. 20, 2014, to Betts-Lacroix et al.
U.S. Appl. No. 14/871,998, filed Sep. 30, 2015, to Betts-Lacroix et al.

* cited by examiner

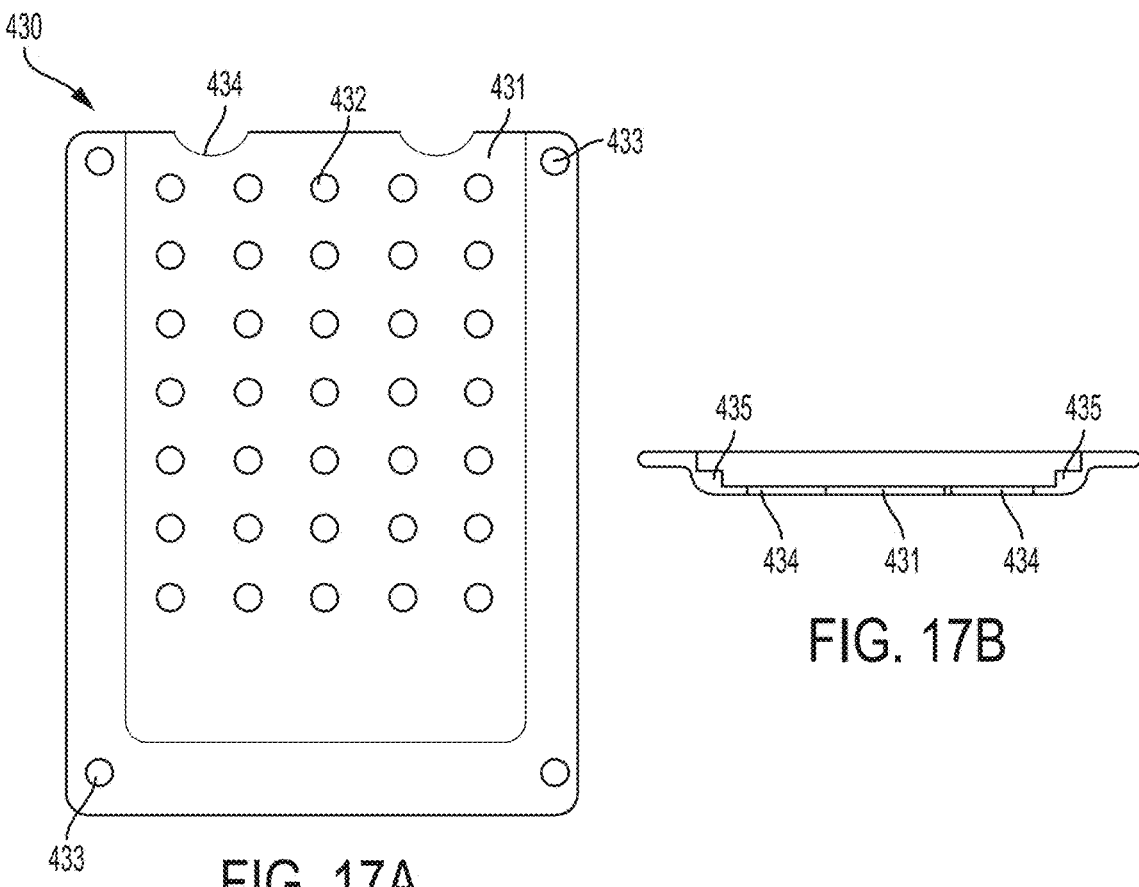
FIG. 17A
FIG. 17B
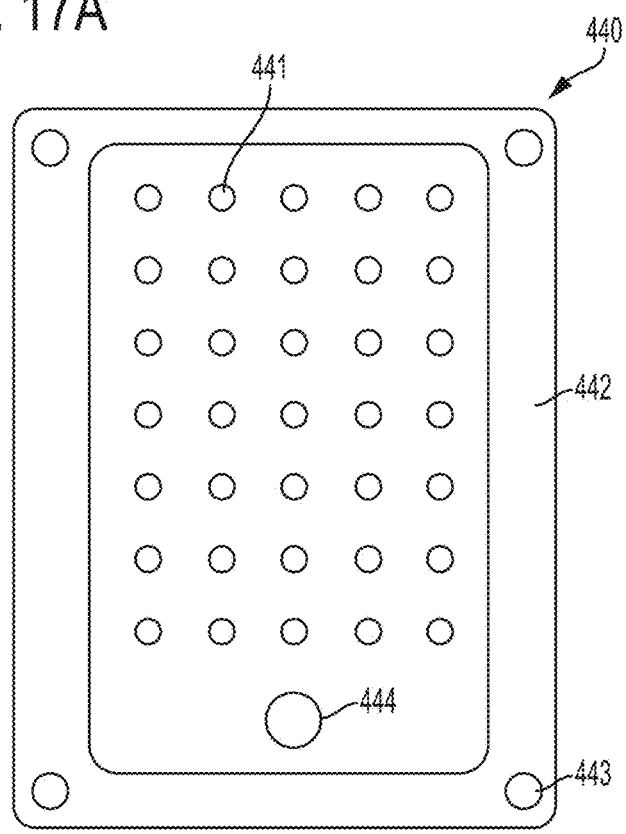
FIG. 17C

DEVICES FOR SELECTIVELY RELEASING VOLATILE COMPOUNDS

TECHNICAL FIELD

This application relates to apparatuses and methods for sequestering and releasing odoriferous compounds into the air and utilizing such technology for research involving experimental animals.

BACKGROUND

Research is commonly performed on experimental animals that are housed in cages. Typically, these experimental animals are small mammals, such as mice or rats. The research may involve, for example, a drug test, a nutritional test, a genetic test, a test of a surgical procedure, an optogenetics test, or another observation of a physiological or behavioral response to a change in environmental condition or other stimulus. The experimental animals may be divided into a control group and one or more experimental groups. The cages in which the animals are housed may be arrayed in racks.

The housed animals are typically checked in two ways: husbandry checks and experimental checks. Husbandry refers to serving the physiological needs of the animals. Husbandry may include observing the wellbeing of the animals, such as, for example, a health check once or twice a day to make sure that none of the animals has developed any symptoms of disease or has died. Health checks may involve looking at the animals through the transparent cage walls in situ without moving the cages, or alternatively pulling the cages partially or completely out of their racks to visually inspect the animals. Experimental checks, meanwhile, are performed to obtain data for the research being conducted. Experimental checks may involve closer examination of the animals than husbandry checks, such as involving opening the cages and removing the animals from the cages. Experimental checks may involve, for example, looking for clinical symptoms in the animals. Experimental checks may also include behavioral tests, such as, for example, water maze or hole board tests, extractions of blood or tissue from the animals, or measurements such as imaging of the animals.

However, the data obtained from checking the animals may have limited value. Since human technicians may be needed to perform the checks and the checks may perturb the animals, these checks are performed only at certain times. Thus, the data typically represents only a relatively small set of data points for any given animal.

Furthermore, physically contacting the animals, such as through opening the animals' cages, removing them from their cages, and performing measurements on them—or even just approaching the cage to view the animal through the bidirectionally transparent wall, or partially sliding the cage containing the animal out of a rack—can physiologically or psychologically perturb the animals. The consequences of these types of perturbations are often not well understood. Furthermore, there may be inconsistencies in the perturbations, such as differences in when and how the human technicians perform checks across different individual animals. The animals' physiological states and behavior may therefore be altered in ways that are difficult to predict and inconsistent between distinct animals. Thus, these measurement techniques can interfere significantly with the quality of the data obtained from the experiment.

The process of checking the experimental animals may also cause contamination of the animal's living space or the testing equipment. This contamination may, in turn, exacerbate the differences in conditions under which the animals are housed. For example, one human technician may introduce one particular foreign odor into one living space, while another human technician introduces a different odor into another living space. The human technicians who are handling animals from different cages, or using common equipment, may also cause cross-contamination between animals in different cages.

In addition, a substantial amount of resources, such as the time and labor of skilled technicians, is expended to monitor the animals. This can account for a significant amount of the total cost of running such an experiment.

Thus, it is desirable to perform checks on experimental animals and provide stimuli to experimental animals in a way that yields high-resolution and reliable data in relation to the number of animals. It is also desirable to avoid physical contact with the animals, inconsistent perturbations of the animals, and cross-contamination between animals in different cages when the animals are checked. Moreover, it is desirable to reduce the amount of time and labor that is expended on running the animal experiment.

SUMMARY

In one embodiment, an apparatus for sequestering and releasing compounds into the air is provided. The apparatus includes a card with a first side and a second side; and a plurality of compound-sequestering structures affixed to the first side. Each of the plurality of compound-sequestering structures is configured to release a compound into the air when heated to a first temperature.

In another embodiment, a heating device for use with a card containing a plurality of compound-sequestering structures is provided. The heating device includes a heating structure with a plurality of heating elements in a spatial array pattern and a controller configured to control each heating element independently. When the heating structure is properly aligned with the corresponding card. The controller is configured to, independently for each of the plurality of compound-sequestering structures, cause a compound-sequestering structure to release compounds into the air by driving a corresponding heating element of the plurality of heating elements to heat the compound-sequestering structure to a particular temperature range for a particular duration.

In yet another embodiment, a heating device for use with a card containing a plurality of compound-sequestering structures is provided. The heating device includes a heating structure comprising a laser; an orientation system configured to mechanically or optically direct an output of the laser; and a controller configured to control both the intensity of the laser and the orientation system. When the heating structure is sufficiently aligned with the corresponding card, the controller is configured to, independently for each of the plurality of compound-sequestering structures, cause a compound-sequestering structure to release compounds into the air by directing the orientation system to align the output of the laser at the compound-sequestering structure and by driving the laser to heat the compound-sequestering structure to a particular temperature for a particular duration.

It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments and aspects of the apparatuses and methods described herein and, together with the description, serve to explain the principles of the invention.

FIGS. 17A-17B are front and top views of an example of an embodiment of a card-receiving apparatus of a compound releasing system.

FIG. 17C is a front view of an example of an embodiment of a heating structure of a compound releasing system.

DETAILED DESCRIPTION

An electronic monitor may be adapted to be removably coupled to a cage housing experimental animals to be positioned in a predefined position relative to the cage and monitor one or more of the experimental animals. The electronic monitor can be adapted to maintain a substantially sterile barrier between the animal living space in the cage and the environment external to the cage while the electronic monitor is coupled to the cage. Sterility refers to chemical and biological isolation from the ambient environment, such as, for example, isolation from foreign odors, soot particles, viruses, parasitic worm eggs, bacteria, prions, proteins, metabolites, parasitic mites and their eggs, and humidity and temperature fluctuations. The electronic monitor can thereby monitor the experimental animals while minimizing perturbations to the animals. Examples of such an electronic monitor are described in U.S. patent application Ser. No. 14/549,403 to Betts-LaCroix et al., which is incorporated herein by reference in its entirety.

Figure 1A:
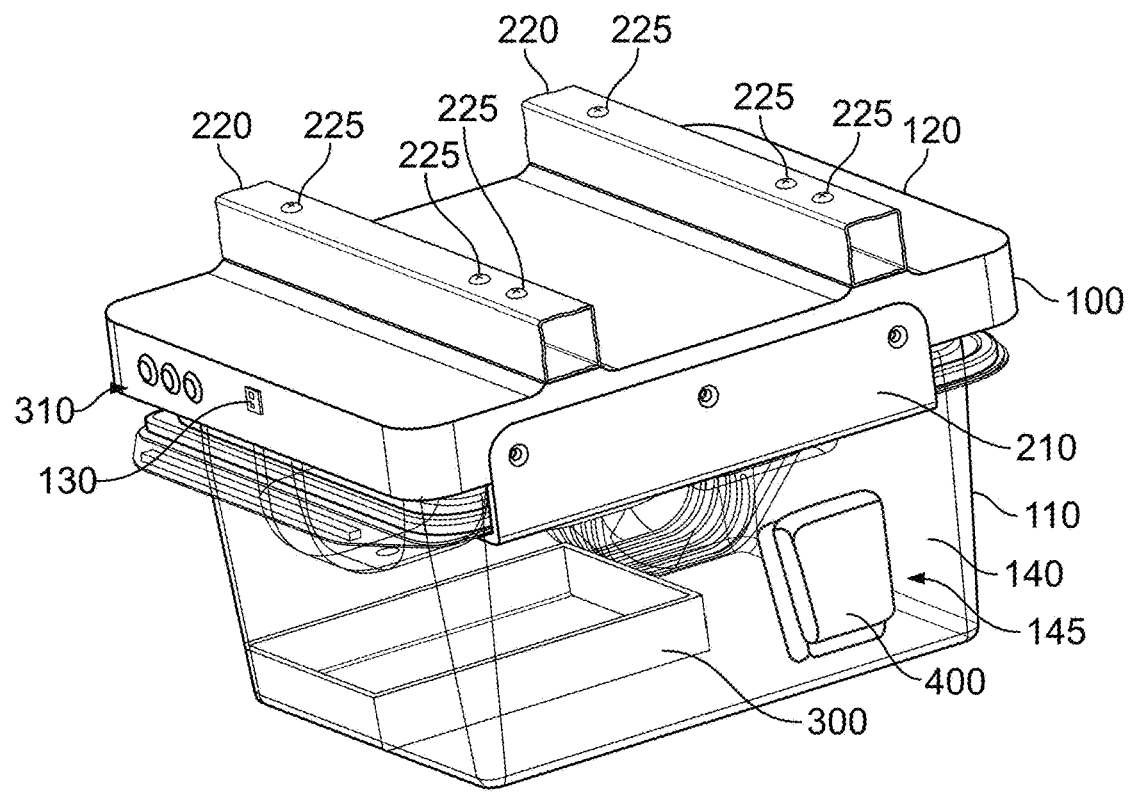
FIGS. 1A and 1B are three-dimensional perspective views an example of an embodiment of an electronic monitor and compound releasing system that is coupled to a cage.
Figure 1B:
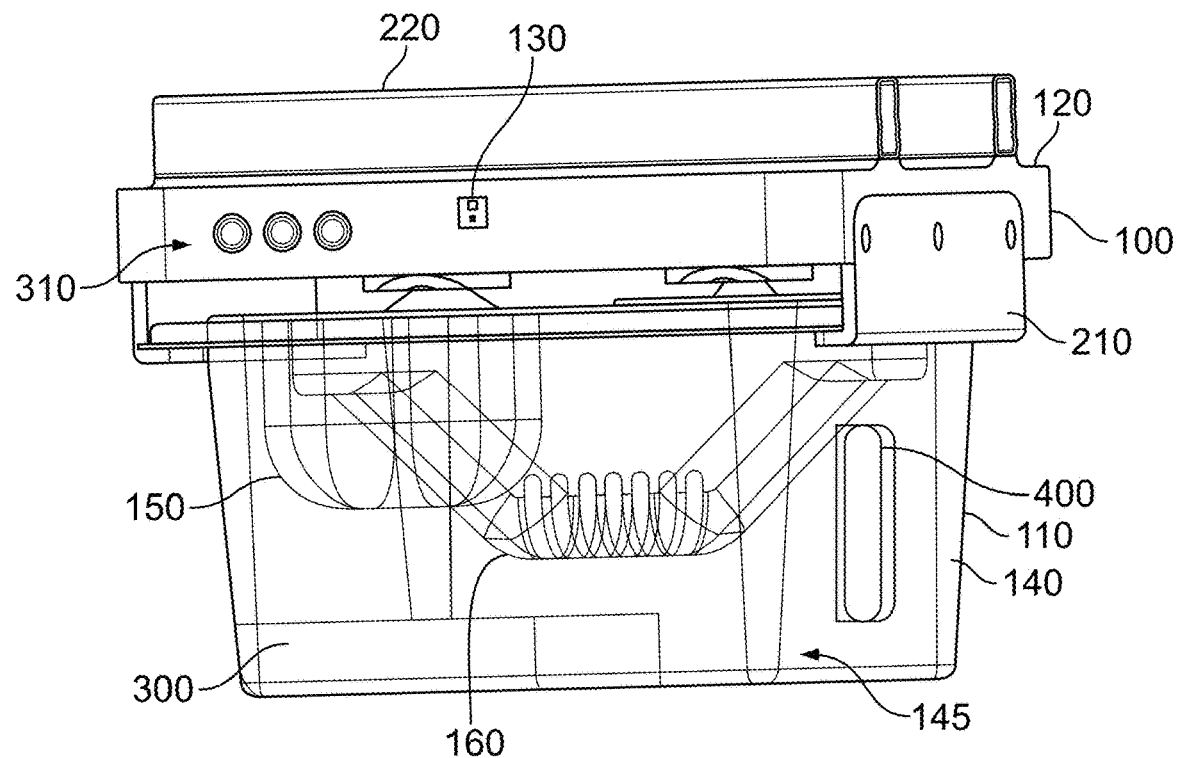

FIGS. 1A and 1B illustrate an example of an embodiment of an electronic monitor 100 and a cage 110 that are mechanically coupled to each other. The embodiment also includes a compound releasing system 400, which, as shown may also be mechanically coupled to cage 110.

Electronic monitor 100 has a housing 120 to which electronic and/or other components of electronic monitor 100 are attached. Housing 120 may form a substantially airtight enclosure around sensitive components of electronic monitor 100. These sensitive components may include, for example, cameras, microphones, electromagnetic sources, electronic circuitry, and optical components such as fiber optics. For example, housing 120 may include one or more seals or gaskets to be capable of maintaining an airtight environment around the key or sensitive components of electronic monitor 100. Electronic monitor 100 may also have one or more ambient sensors 130 to determine characteristics of the environment outside cage 110. Ambient sensors 130 may determine, for example, an outside light level or temperature, or to detect ambient sound.

Cage 110 has one or more walls 140 that enclose living space 145 of the experimental animals. In one embodiment, walls 140 define a living space 145 that is approximately a rectangular prism. In other embodiments, however, walls 140 may have other shapes or dimensions. In illustrative examples, a mouse cage may be shaped and sized to house from one to about five mice, while a rat cage may be capable of housing up to about 10 mice. For example, mice may be housed singly or in pairs. In one embodiment, walls 140 of cage 110 enclose a substantially cuboid living space 145 of at least 10 cm×10 cm×5 cm.

Cage 110 may also include shaped features to provide water and/or food to the experimental animals. For example, cage 110 may have a water dispenser 150. Cage 110 may also have a food dispenser 160. If cage 110 is of a disposable type, then water dispenser 150 and/or food dispenser 160 may be pre-filled with an amount of water or food corresponding to an expected lifespan of the animals, an expected timespan of an experiment, or a given interval between cage changes. A given interval between cage changes may be, for example, one, two, or four weeks, such as may be suitable for the particular types of cage, animal, and experiment.

Compound releasing system 400 may be included to release various compounds into the atmosphere of living space 145 without otherwise disturbing the experimental animals. As used herein, "compound" comprise single molecular compounds or may comprise multiple molecular compounds in a solution or mixture. Such compounds may comprise various olfactory stimuli detectable by the laboratory animals, such as, for example, female or male rodent urine, rodent predator scents, various food scents, or other types of scents that may be novel to a laboratory animal. During animal research, such olfactory stimuli may serve to reward an animal, or serve as a basis to assess an animal's behavior or cognition. In other embodiments, the compound releasing system may deliver a drug to an experimental animal.

Figure 2A:
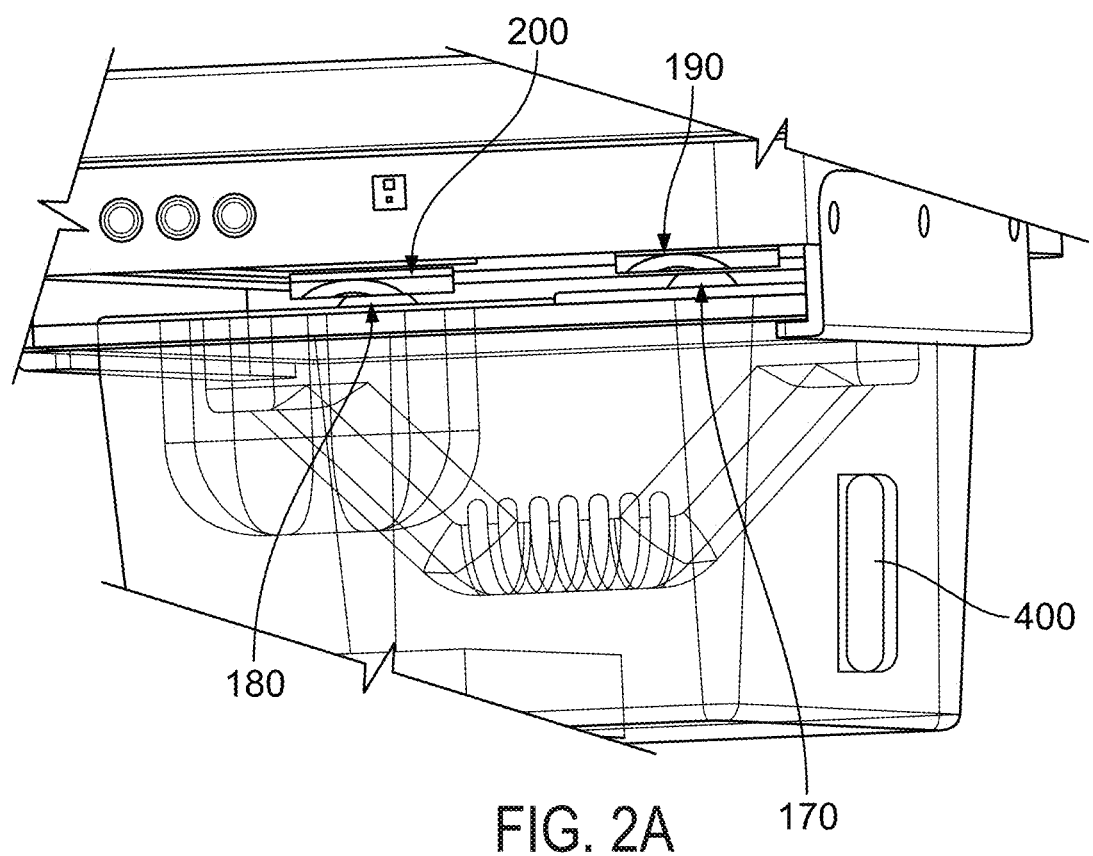
FIGS. 2A and 2B are three-dimensional perspective views of an example of an embodiment of an electronic monitor coupled to the cage that is illustrated in FIGS. 1A and 1B.
Figure 2B:
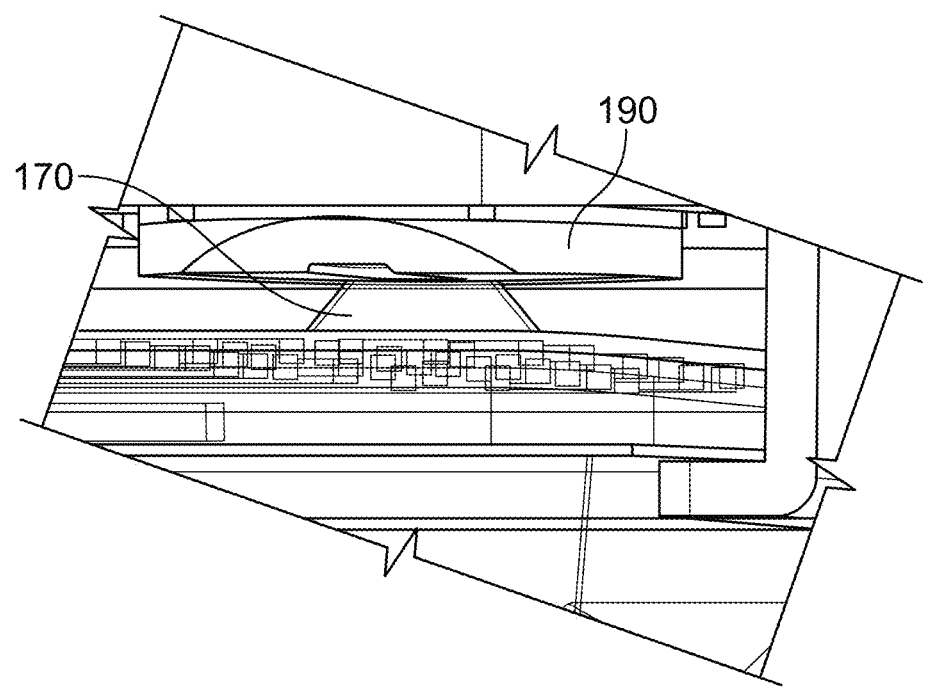

Cage 110 may include at least one air inlet for clean air, and at least one air outlet for contaminated air. In one example, illustrated in FIGS. 2A and 2B, cage 110 has air nipples 170, 180 that structurally complement air inlet 190 and air outlet 200, respectively. Air inlet 190 and air outlet 200 may couple to an external air supply conduit and an air exhaust conduit, respectively.

Electronic monitors 100 may be structurally adapted to permit easy and fast uncoupling of cages 110 from electronic monitors 100 by a human technician or even by a robot. For example, electronic monitors 100 may be structurally adapted to permit coupling and uncoupling by sliding cages 110 into and out of electronic monitors 100. Returning to FIGS. 1A and 1B, in one version, electronic monitors 100 have arms 210 extending from housing 120 to support cages 110, such as for example L-shaped arms 210 extending from under housing 120 to stably hold cages 110 underneath housing 120. Furthermore, when a cage 110 is slid into electronic monitor 100, air nipples 170, 180 may mechanically snap into air inlet 190 and air outlet 200, respectively, to create substantially sealed air channels and hold cage 110 in place with respect to electronic monitor 100.

Multiple cages 110 that are coupled to respective electronic monitors 100 may be mechanically supported in arrays by a rack. Cages 110 may be supported by the rack by nonpermanent mechanical coupling, such that they can be easily removed from the rack if desired. For example, electronic monitors 100 may be supported by mounting rails 220 of the rack to stably hang electronic monitors 100 from the rack (or, in alternative versions that are not illustrated here, electronic monitors 100 may attach to mounting rails 220 from a side of electronic monitors 100 or even underneath cage 110). Electronic monitors 100, in this example, may be attached to mounting rails 220 of the rack by bolts 225 that pass through holes in rails 220.

The rack may also structurally provide one or more resources used in the cage, such as, for example, conveying clean air and exhausting used air, electrical power, electrical or optical signals, water, and nutrients for the experimental animals. For example, an air supply conduit and an air exhaust conduit adapted attach to cage 110 may extend from the cage rack or even constitute part of the rack itself. Similarly, electrical wiring for power and transmission of signals may be extended inside or along the beams of the rack and connect to electronic monitors 100, such as via complementary ports, for example through respective "male" and "female" connectors, on electronic monitors 100 and the rack.

Figure 3:
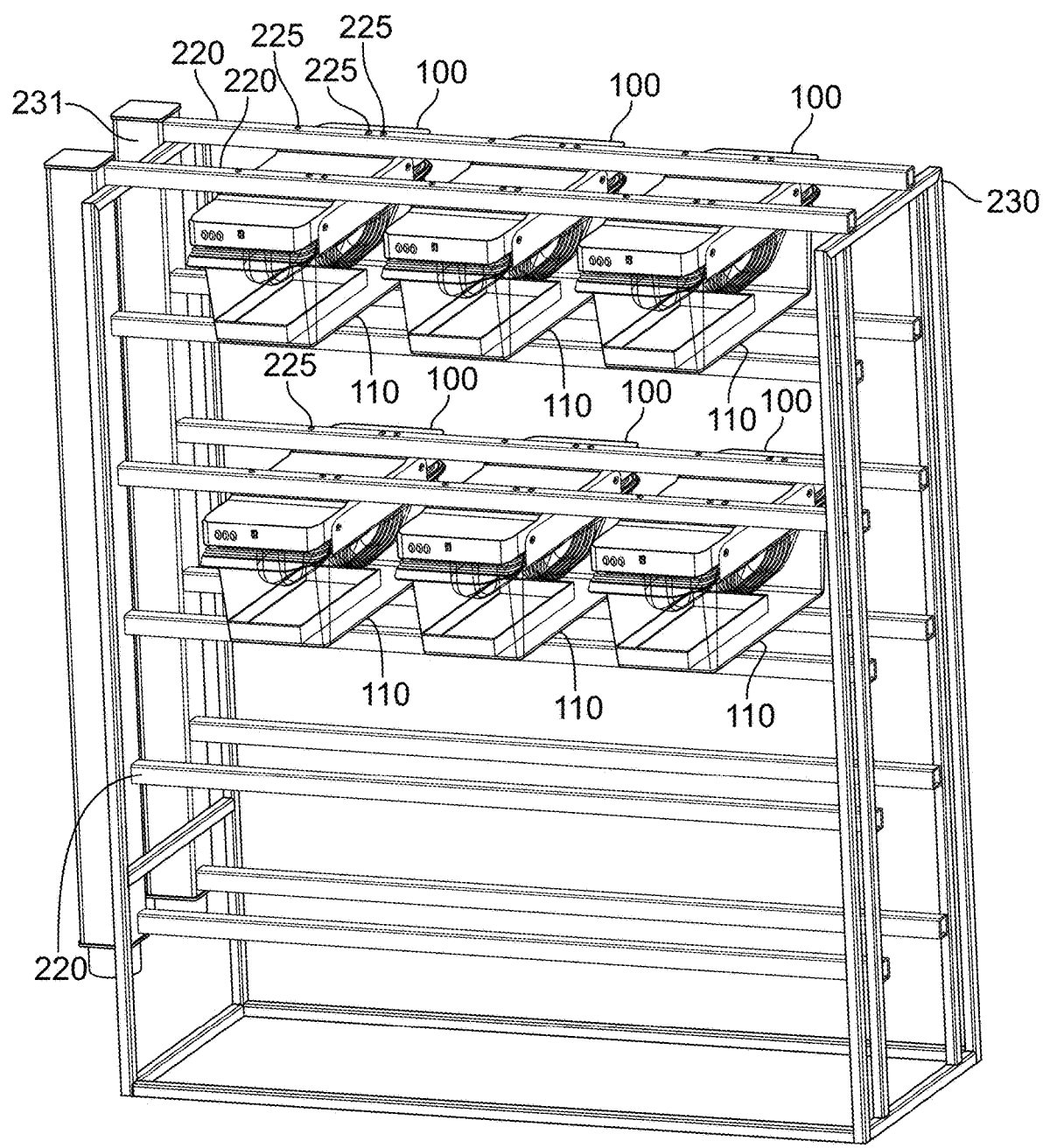
FIG. 3 is a three-dimensional perspective view of an example of an embodiment of a rack having multiple electronic monitors coupled to respective cages and arranged in a two-dimensional rectilinear grid array.

In certain embodiments, the rack supports the cages in a two-dimensional or three-dimensional rectilinear grid array. FIG. 3 illustrates an example of an embodiment of a rack 230 that supports multiple cages 110 coupled to respective electronic monitors 100, which are arranged in the rack in a two-dimensional rectilinear grid array. However, racks may be implemented that support other suitable assemblages of cages 110. For example, a rack may be adapted to allow cages 110 to be stacked in a rotatable cylindrical array. In other examples, the rack may be adapted to stack cages 110 in hexagonal, diagonal, or other configurations. Mounting rails 220 of rack 230, as depicted in FIG. 3, may include or support horizontal air supply plenums that are part of an air supply conduit, and each horizontal air plenum may receive supplied clean air from a vertical air plenum 231 of rack 230. Although not depicted in FIG. 3, some or all of cages 110 in rack 230 may include compound releasing system 400, which may be attached to a side wall 140 of cage(s) 110 or may be included in an air supply pod 450 of cage(s) 110 that receives air from the air supply conduit.

Figure 4:
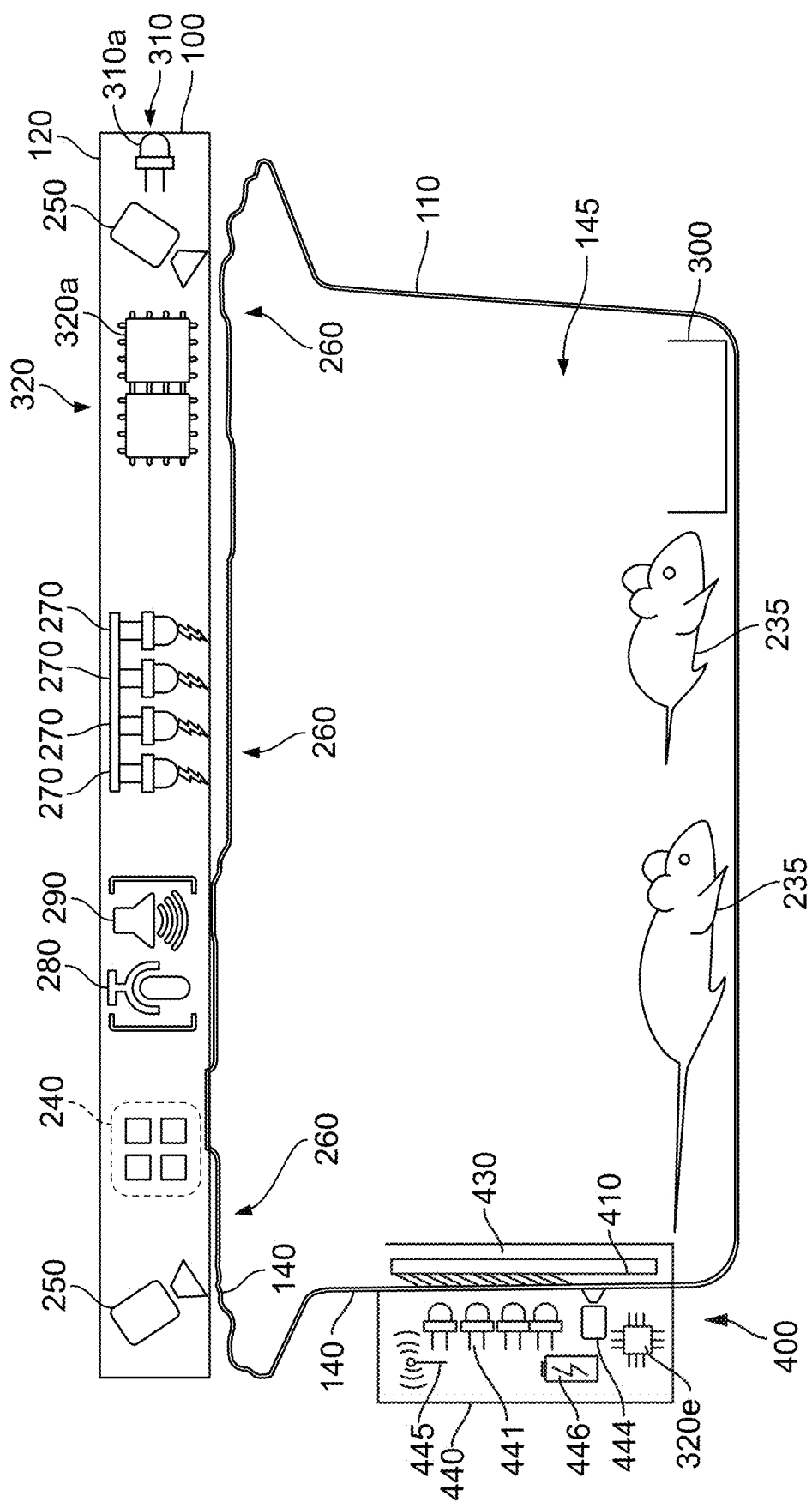
FIG. 4 is a schematic illustration side view of an example of an embodiment of an electronic monitor and compound releasing system coupled to a cage.

FIG. 4 is a schematic illustration of a side view of an example of an embodiment of a compound releasing system 400 and an electronic monitor 100 coupled to a cage 110 that houses experimental animals 235. Compound releasing system 400 may include a card apparatus 410 that contains sequestered compounds, a card-receiving element 430, and a heating structure 440 that selectively heats regions of card apparatus 410 to release compounds into the atmosphere of living space 145.

As depicted in FIGS. 16A-E, card apparatus 410 may sequester compounds in a compound-sequestering emulsion (s) deposited on a card 415. Such emulsion(s) may include a volatile phase that is encapsulated in a waxy phase. In addition to waxes, the waxy phase may comprise other substances that have a phase transition that permits higher mobility in specific temperature ranges. For example, the waxy phase may comprise a substantially hydrophobic polymer in some embodiments. Card 415 may comprise a substrate with a thermal conductivity of less than 1 W/m·K, and may include, for example, paper, plastic, cloth, felt, and/or wood. Although card 415 is depicted as rectangular, it can be any shape suitable for its purpose, including any circle, oval, polygon, donut shape, or combination thereof. The volatile phase, which may include the sequestered compound, may be encapsulated in a waxy phase such that the volatile phase is exposed to the atmosphere only when the waxy phase is sufficiently melted. The volatile phase is preferably hydrophilic and may include water and/or alcohols. Preferably, the volatile phase may be formed as microvesicles 416 that are completely surrounded by an encapsulate 414 made of waxy phase. In some embodiments, the volatile phase may include an alcohol-based solution into which a sequestered compound is dissolved. In other embodiments, the volatile phase may include a carrier solution with a low boiling point, such as a low-molecular-weight hydrocarbon or alcohol, and a sequestered compound. The compound may, for example, be an odiferous compound or a drug, such as a trace amine type hormone. The waxy phase preferably has a precise melting point or melting point range, for example, between 28° C. and 54° C. For example, the waxy phase may comprise Octadecane, Nonadecane, Icosane, Heneicosane, Docosane, Tricosane, and/or Tetracosane.

Figure 16A:
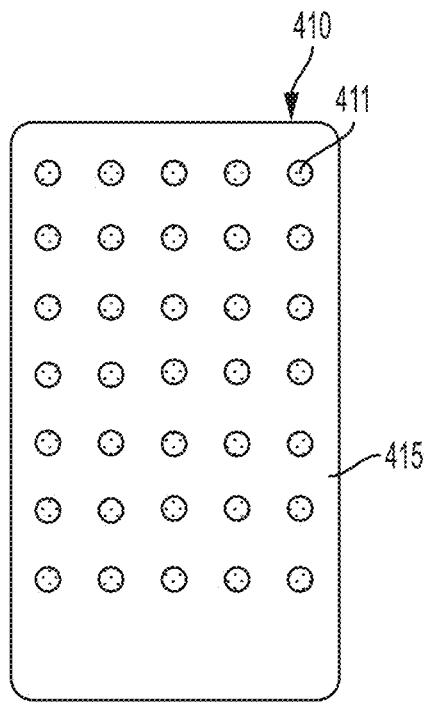
FIGS. 16A-16D are front, back, top, and magnified top views of an example of an embodiment of card apparatus of a compound releasing system.

FIGS. 16A-D illustrate an embodiment of card apparatus 410 that includes a plurality of compound-sequestering structures 411. For example, FIG. 16A depicts a front view a card apparatus 410 where compound-sequestering structures 411 are arranged in a spatial array comprising several columns. Each compound-sequestering structure 411 may be a waxy blob that includes microvesicles 416 surrounded by encapsulant 414, as depicted in detail in FIG. 16D. The compound-sequestering structures 411 may contain a variety of different sequestered compounds, and in some embodiments, all structures 411 within any given column may contain the same sequestered compound to avoid potential commingling of compounds when compound-sequestering structures 411 are melted. The encapsulant 414 of the various compound-sequestering structures 411 in a given card apparatus 410 may have the same melting point range or may have a different melting point range.

Figure 16B:
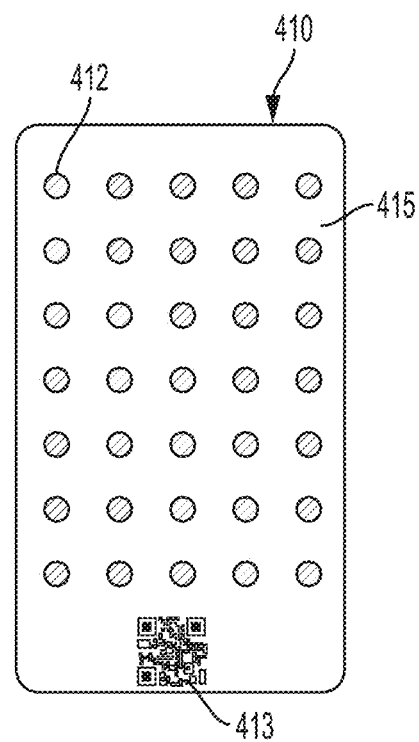
Figure 16C:
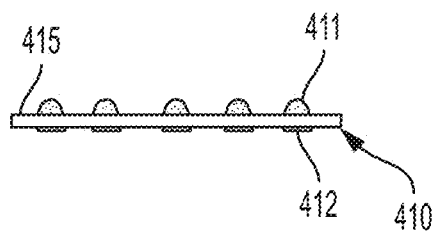
Figure 16D:
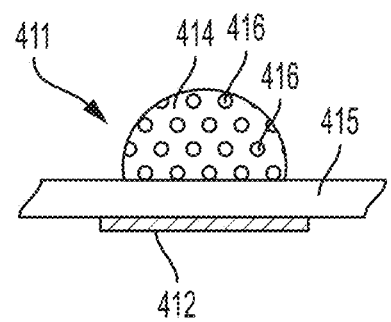

FIGS. 16B, 16C, and 16D depict back, top, and magnified top views of a card apparatus 410. As illustrated, the back of a card apparatus 410 may include heat receiving elements 412 that are aligned behind compound-sequestering structures 411 to improve heat conductivity. In other embodiments, heat receiving elements 412 may be located directly underneath compound-sequestering structures 411. Heat receiving elements 412 may be metallic and may be printed onto the card during manufacture, or alternatively may be embedded within a card. The back of card apparatus 410 may further include a marking 413, such as a QR code, a bar code, or other computer-readable marking, to provide information about the card apparatus 410 and/or assist in determining the precise position of the card apparatus 410. For example, marking 413 may include information regarding the type, location, or concentration of sequestered compound(s) on the card apparatus 410; wax encapsulant 414 melting temperature range(s); or an expiration date. Other embodiments of card apparatus 410 may include additional features between compound-sequestering structures 411, such as insulating plastic foam or gaps within card 415, to reduce the potential for heat conductivity and inadvertent melting of compound-sequestering structures 411. The insulating foam may be located on the front and/or back of card 415. The gap(s) may be sections of a card 415 where material has been removed. In alternative embodiments, the plurality of compound-sequestering structures 411 may be located on the back of card apparatus 410 such that the structures 411 directly face heating structure 440.

FIGS. 17A and 17B depict front and top views, respectively, of an embodiment of card-receiving element 430. Card-receiving element 430 may secure card apparatus 410 to the inside of wall 140 and position it such that its sequestered compounds may be selectively released by heating structure 440. Card-receiving element 431 may include a pocket 431 into which a sufficiently rigid card 415 may be slid. The pocket 431 may be constructed from a hard plastic or metal to prevent an experimental animal from chewing through or otherwise damaging it. In an embodiment, pocket 431 includes pocket holes 432 that preferably align with compound-sequestering structures 411 when card apparatus 410 is properly inserted into pocket 431. The pocket holes may provide a direct route for released compounds to enter the atmosphere of the living space. Alternatively, the card-receiving element 430 can include a metal or hard plastic grate to both protect a card apparatus 410 from laboratory animals and allow released compounds to disperse. The top of card-receiving element 430 may also include one or more notches 434 to make it easier to insert and remove card apparatus 410. Additionally, card-receiving element 430 may include one or more spacers 435 that are configure to secure the edges of card 415 while preventing the compound-sequestering emulsion(s) from either contacting pocket 431 (or a grate) or being placed within reach of the experimental animals. Card-receiving element 430 may be fastened to wall 140 via pins 403 through pin holes 433.

FIG. 17C depicts an embodiment of heating structure 440 from the front. As depicted, heating structure 440 includes a plurality of heating elements 441. The heating elements 441 may be IR LEDs, coils or other electrically resistive elements, incandescent bulbs, or lasers, such as an IR laser. IR LEDs may be preferred because they are relatively cheap, relatively small, draw relatively little power, and are easy to control with precision. In the depicted embodiment, heating elements 441 are configured to align with the plurality of compound-sequestering structures 411 and/or heat receiving elements 412 of card apparatus 410. Heating structure 440 may include heating structure camera 444 to capture an image of markings 413 or other characteristics of card apparatus 410. Heating structure 440 may further include heating structure body 442 to house additional electrical or electromechanical components. With reference to FIG. 4, these components may include a heating structure controller 320e (which, as noted below, may be or may be a part of controller 320); a battery 446 or other power source for the heat structure; a data communication element 445, which may include a radio antenna, an IR receiver, an IR transmitter, or any other suitable communication device known in the art; and other standard electrical circuit components. The components may also include one or more thermistors or other temperature measuring devices (not shown).

Controller 320e may control each heating element 441 independently, such that each heating element is driven (1) at an appropriate juncture, (2) with an appropriate amount of power to melt the encapsulant wax 414 of each compound-sequestering structure 411 without releasing compounds of adjacent structures 411, and (3) for an appropriate duration. For example, for IR LEDs, incandescent bulbs, and lasers, controller 320e may control an intensity of radiation emitted from each heating element 441. When compound releasing structures 411 are arranged in columns, controller 320e may control heating elements 441 such that the structures 411 in each column are melted from lowest to highest in order to reduce the potential of melted encapsulant wax 414 dripping onto any intact, unheated structures 411. In other embodiments controller 320e may control heating elements 441 such that the structures 411 in each column are melted from highest to lowest in order to reduce the potential of rising heat from the heating elements from compromising any intact, unheated structures 411. Controller 320e may control camera 444. Controller 320e may also control data communication element 445 to communicate with other components of controller 320 to receive instructions or data for control of heating elements 441; report errors or warnings; and send captured images of card apparatus 410, which may include images of markings 413. In alternative embodiments, for example where heating structure 440 may be connected to a power source of electronic monitor 100 or the rack, battery 446 may be omitted. Similarly, in alternative embodiments, for example where controller 320a or another controller 320 element is wired to heating structure 440, data communication element 445 and/or controller 320e may be omitted.

Figure 17D:
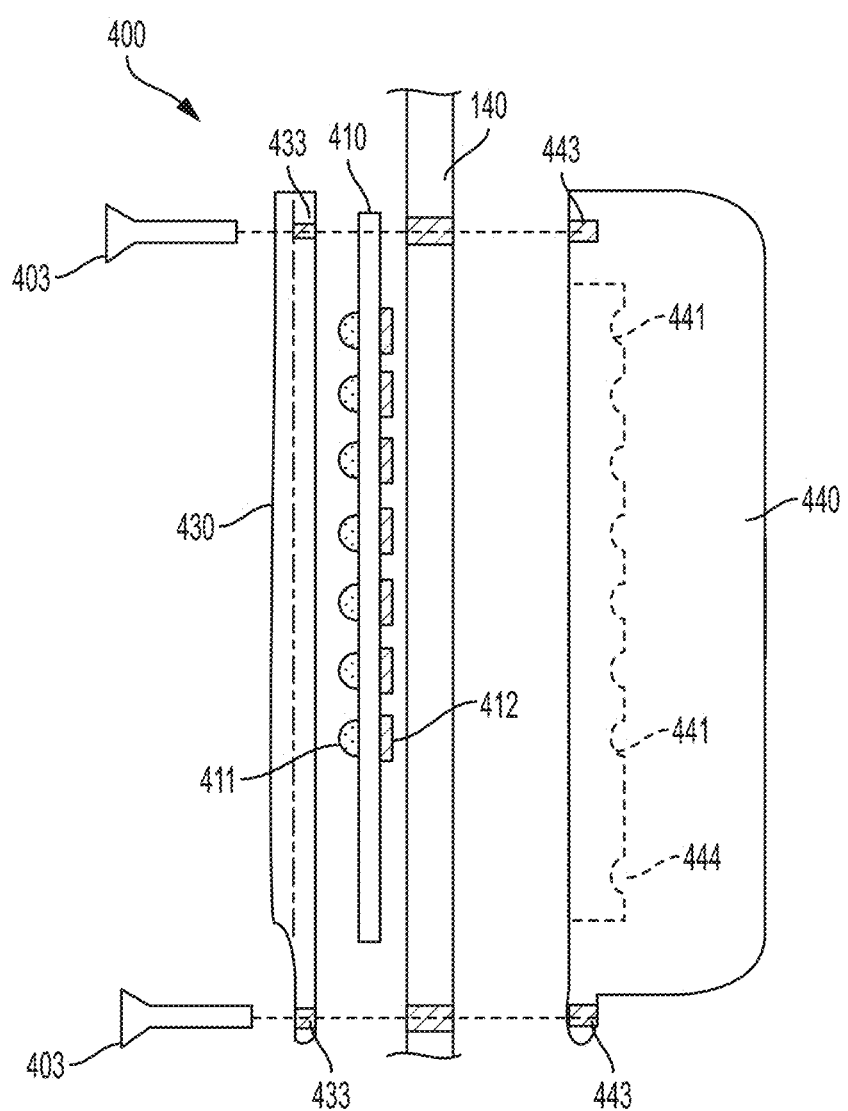
FIG. 17D is an exploded side view of an example of an embodiment of a compound releasing system.

FIG. 17D depicts an exploded view of an embodiment of heating system 400. Heating structure 440 may be fastened to wall 140 via pins 403 through pin holes 443. Because, in some embodiments, the same pins 403 may also fasten card-receiving element 430 to wall 140, the pins may serve to align card-receiving element 430 and heating structure 440. In turn, card apparatus 410 may be aligned with heating structure 440 by virtue of a snug fit of pocket 431 around card apparatus 410. Pins 403 may be machine screws, bolts, or any other suitable mechanical device and may pass through drilled or integrally formed holes in wall 140. An image of markings 413 taken by camera 444 can confirm proper alignment. In some embodiments (not shown), card apparatus 410 may include pin holes that correspond with the pin holes 433 and 443 to improve reliability of alignment.

In addition to the embodiment depicted in FIG. 17D, heating system 400 may be coupled with cage 110 in a variety of other ways. For example, heating structure 440 may be attached to an arm 210 of an electronic monitor 100; may be attached to a rail 220 of rack 230; may be attached to a wall 140 via glue, screw, or other mechanical fastener; may be, at least in part, formed integrally with wall 140; or may be included in electronic monitor 100.

Card-receiving element 430 may be attached to a wall 140 via glue, screw, or other mechanical fastener; may be, at least in part, formed integrally with wall 140; or may be included in electronic monitor 100. Card-receiving element 430 may, in some embodiments, omit pocket 431 and comprise grooves, hooks, clamps, clips, snaps, bolts, pins, screws, or other mechanical elements to secure card apparatus 110. It may be desirable to use a positioning jig when installing card-receiving element 430 on the inside of wall 140 to help reliably achieve alignment with heating structure 440, optimal placement within cage 110, and/or uniform placement among cages 110.

Some embodiments of card apparatus 410 may include an adhesive such that it may be stuck to wall 140 like a sticker. The adhesive may be included on the back of card apparatus 410 near its edges. In some embodiments, for example where the cage is intended to be reusable, the adhesive may be weaker to permit later removal of the card apparatus 410 without difficulty. In other embodiments, for example where the cage is intended to be disposed of after a single use, the adhesive may be stronger to allow a more permanent attachment. Card apparatus 410 may further include a protective layer of hard plastic or metal; the protective layer may include holes or other gaps, or may comprise a grate to allow for compound dispersion while protecting the card apparatus from experimental animals. In these embodiments, card-receiving element 430 may comprise a portion of wall 140 with alignment markings or even just a portion of a wall 140 without alignment markings.

Figure 18:
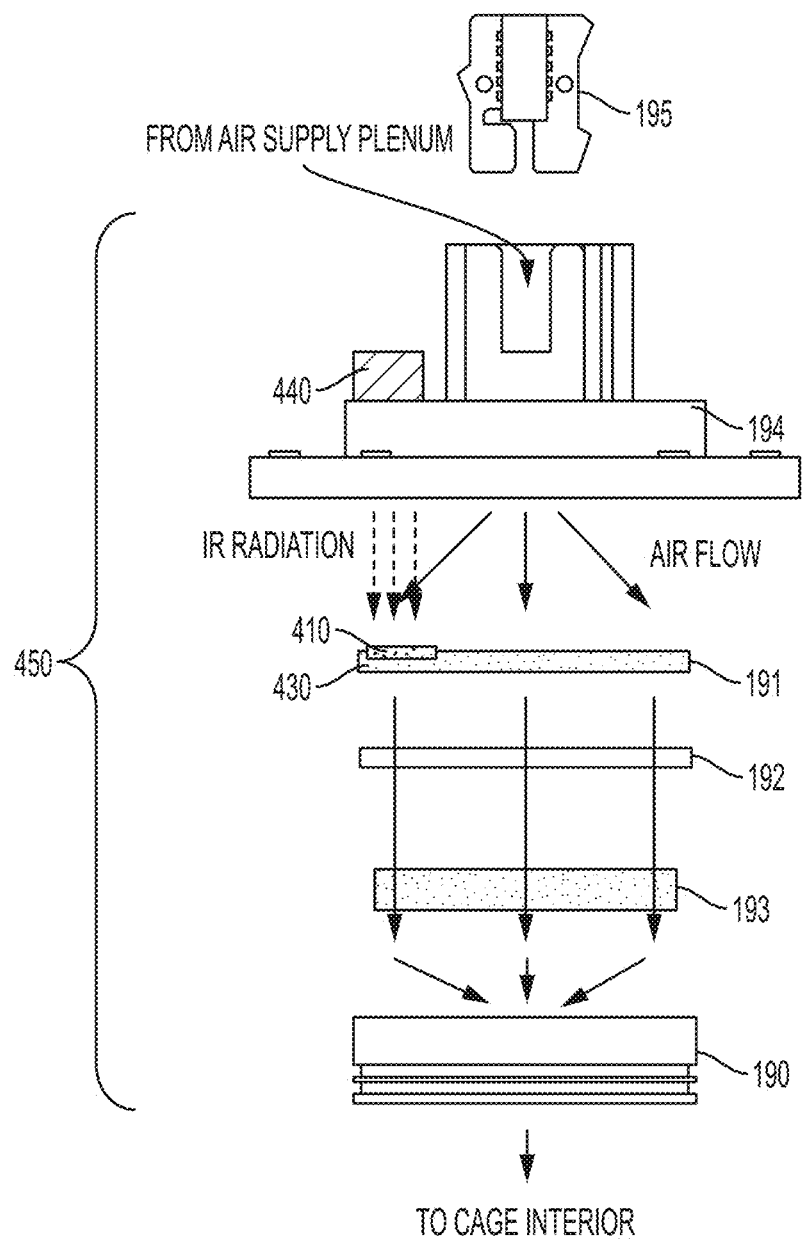
FIG. 18 is an exploded side view of an example of an embodiment of a compound releasing air pod assembly.

As depicted in FIG. 18, some embodiments of compound releasing system 400 may be included in a compound releasing air supply pod 450 that supplies clean air to the cage 110 through air inlet 190. Compound releasing air supply pod 450 may include air receiving portion 194; filters 191, 192, and 193; air inlet 190; heating structure 440; card-receiving element 430; and card apparatus 410. Filter 191 may include card-receiving element 430. Filters 191 and 193 may be coarse filters and filter 192 may be a fine filter. When compound releasing air supply pod 450 is assembled, heating structure 440, card-receiving element 430, and card apparatus 410 may operate in a manner similar or identical to other embodiments of compound releasing system 400 discussed in this disclosure. Air provided to cage 110 through air inlet 190 may then contain sequestered compounds released from card apparatus 410. Air receiving portion 194 may be configured to engage with an air supply plenum connector 195 of a horizontal air supply plenum to receive air from the horizontal air supply plenum.

Figure 14:
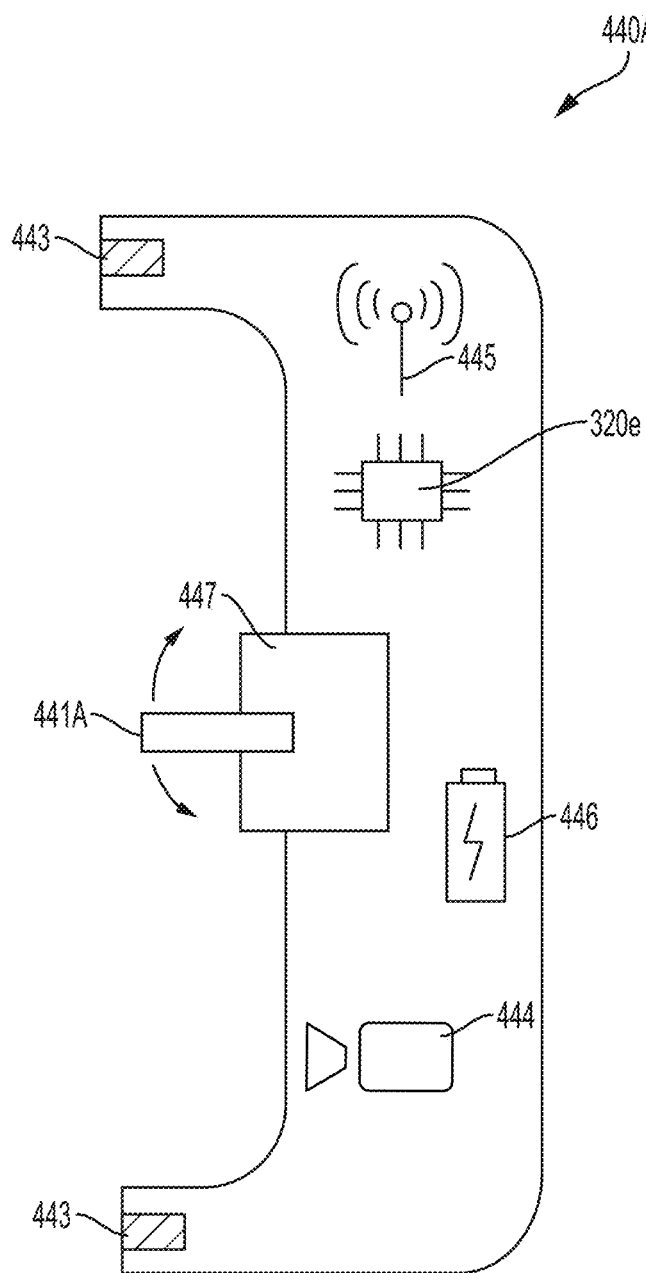
FIG. 14 is a schematic illustration side view of an example of an embodiment of a heating structure of a compound releasing system.

As depicted in FIG. 14, some embodiments of heating structure 440 may be single element heating structures 440A, which may include a single heating element 441A, and an electromechanical orientation system 447 to move and/or or align the single heating element 441A to selectively heat one compound-sequestering structure 411 at a time. Preferably, single heating element 441A may be an IR laser with an output that is directed by the electromechanical orientation system 447 by moving the laser up, down, left and/or right to a position aligned with a selected compound-sequestering structure 411; by moving a portion of the laser to alter its output angle; and/or by moving a set of one or more controllable mirrors to direct the laser output to a specific position on card apparatus 410. Alternatively, single heating element 441A may be an IR LED, electrically resistive element, incandescent bulb, or other suitable heating component known in the art that may be moved by electromechanical orientation system 447. Electromechanical orientation system 447 may be constructed with elements known in the art, for example servo motors and digital encoders, and controlled by controller 320e (or 320). The single heating element 441A may also be controlled by controller 320e (or 320). Camera 444 may be used to capture an image of markings 413. Markings 413 may include fiducial markings that can be used accurately indicate the relative positions of camera 444 and the fiducial markings. Thus, controller 320e (or 320) may process a captured image of a fiducial markings 413 to determine the relative position of heating structure 440A with respect to card apparatus 410 and orient the output of single heating element 441A accordingly. In this manner, single heating element 441A may be targeted to heat an appropriate compound-sequestering structure 411 with precision, even if the placement of card apparatus 410 on wall 140 is not optimal.

In alternative embodiments, a heating structure 440 with an array of heating elements 441 may utilize fiducial markings 413 to confirm an appropriate relative position of heating structure 440 with respect to card apparatus 410. A heating structure 440 with an array of heating elements 441 may also include one or more electromechanical orientation systems 447 (e.g., for individual heating elements 441, the array at large, or a subset of elements 441) controlled by controller 320e (or 320) to position or orient the heating elements 441 to align with respective corresponding sequestering structures 411. Use of camera 444 and markings 413 may further serve this function.

Figure 16E:
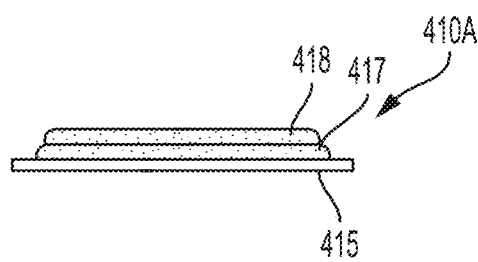
FIG. 16E is a top view of an example of another embodiment of a card apparatus of a compound releasing system.

FIG. 16E depicts an embodiment of card apparatus 410A where the compound-sequestering emulsion is deposited in one or more layers, for example, first compound-sequestering layer 417. A compound-sequestering layer may be considered to be a compound-sequestering structure. A compound-sequestering layer may be of a coating of a substantially uniform thickness, for example of about 0.5 mm to about 2.0 mm. Controller 320e may control one or more heating elements 441 or single heating element 441A to heat a selected area of card apparatus 410 for a specified amount of time and with a specified intensity to cause the encapsulant wax 414 to achieve a particular temperature and release a desired amount of sequestered compound. Controller 320e (or 320) may determine the selected area, specified amount of heating time, and specified heating power through calculations and/or look-up tables that take into account the melting point and thickness of encapsulant wax 414, the concentration of sequestered compound in the emulsion, the type or types of emulsions and their locations on the card apparatus 410, the degree to which and location (s) where card apparatus 410 was already heated, the ambient temperature, and/or additional variables. Some of this information may be supplied in a markings 413 on card apparatus 410 and/or may be otherwise input into or recalled by controller 320e (or 320). Controller 320e (or 320) may be programmed such that bottom portions of card apparatus 410A may be heated before upper portions to avoid potential complications caused by dripping melted encapsulant wax 414.

As shown in FIG. 16E, layers 417 and 418, and, perhaps, additional layers, may be deposited on top of one another. In such embodiments, the compound-sequestering emulsions may be deposited on the back of card 415 such that the compound-sequestering emulsions may directly face heating structure 440. In this manner, heating apparatus 400 may first release compounds from an uppermost layer 418 and subsequently release compounds from a lower layer 417 in a second pass. This configuration may avoid a circumstance where a lower layer 417 is heated first through card 415 and its released compounds would remain trapped by an upper layer 418. Layers 417 and 418 may include the same compounds in different concentrations, may include the same compounds in the same concentration, or may include different compounds. Layers 417 and 418 may include the same encapsulant wax 414 with a single melting point range, or may respectively include encapsulant waxes 414 with different melting point ranges. For example it may be desirable to have a lower layer 417 with a higher melting point that upper layer 418 to prevent lower layer 417 from accidentally melting when upper layer 418 is heated. Layers 417, and 418 and, perhaps, additional layers, may alternatively or additionally be deposited side-by-side on card 415.

Figure 5:
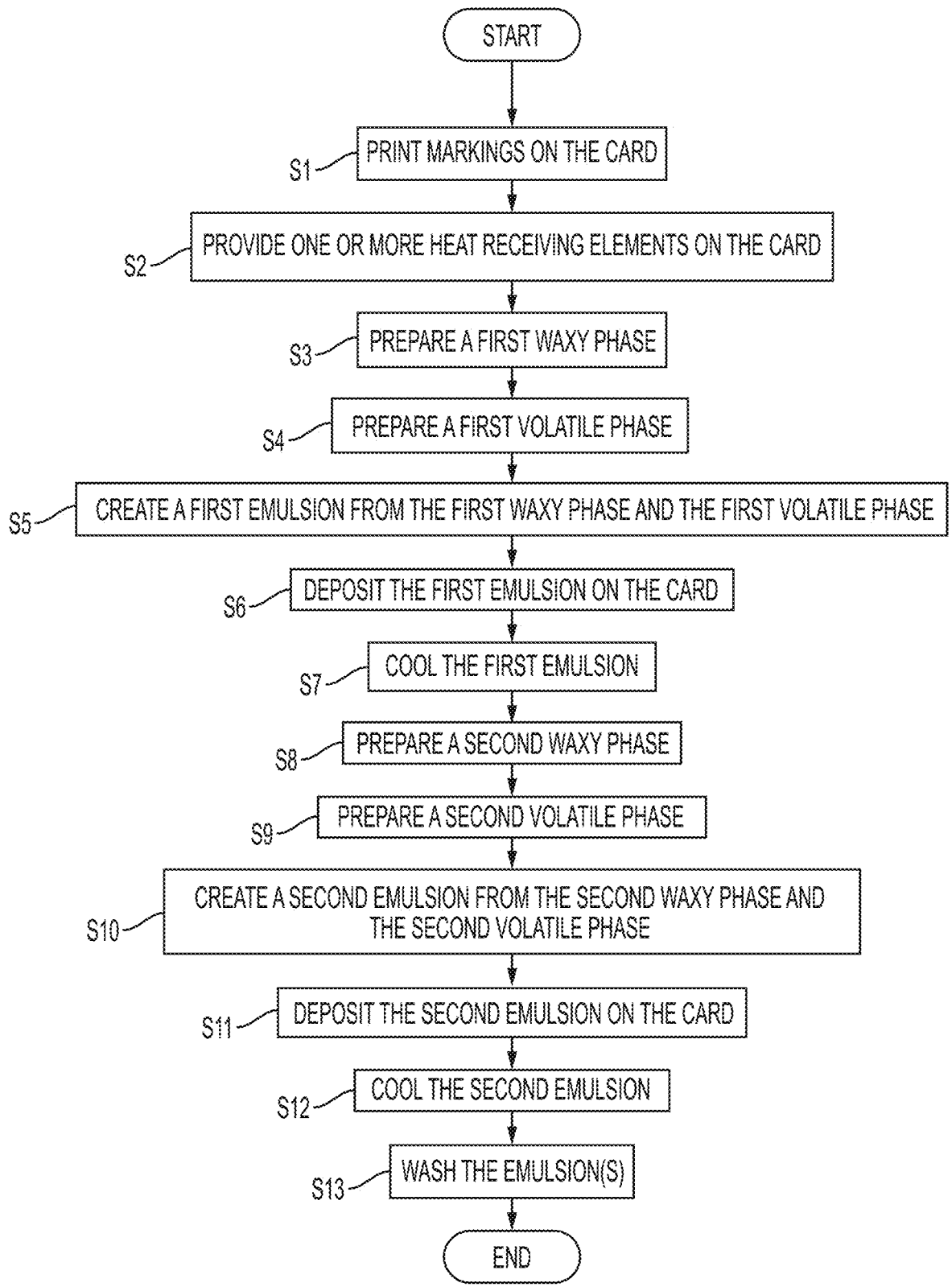
FIG. 5 is a flowchart of an example of an embodiment of a process of manufacturing a card apparatus of a compound releasing system.

FIG. 5 is a flowchart of a version of a process of manufacturing embodiments of card apparatus 410. Depending on the desired characteristics of the card, some steps may be omitted, altered, or reordered. As in step S1, markings 413 may be printed on a card 415. Markings 413 may be computer readable and may include, for example, fiducial markings, information regarding the layout of card apparatus 410, information regarding sequestered compounds, and/or wax encapsulants 414. As in step S2, one or more heat receiving elements 412 may be provided on card 415. The heat receiving elements 412 may be metallic and printed onto card 415.

As in step S3, a first waxy phase 414 is prepared. The first waxy phase may be prepared by melting a wax with a narrow melting point range. As in step S4, a first volatile phase that includes a first compound to be sequestered is prepared. As in step S5, a first emulsion is created from the first waxy phase and the first volatile phase. This first emulsion may be made by vigorously mixing the first waxy phase and the first volatile phase into a colloidal suspension such that the first volatile phase forms microvesicles within the first waxy phase. A sonicator or nebulizer may be used in creating the first emulsion. As in step S6, the first emulsion may be deposited on the card. The first emulsion may be deposited as droplets. In some embodiments, each droplet may contain approximately 20 mL of a compound, such as a scented extract. If heat receiving elements 412 are included, the first emulsion may be applied opposite from (e.g., on the other side of card 415) or directly on top of heat receiving elements 412. The first emulsion may alternatively be deposited as a layer 417. As in step S7, the first emulsion is cooled. Rapid cooling may be preferred to prevent microvesicles from rising to the surface of the deposited emulsion such that portions of volatile phase are freed from the waxy encapsulant 414. For example, the first emulsion may be exposed to below freezing temperatures to accomplish rapid cooling.

As in Step S8, a second waxy phase is prepared. The second waxy phase may be the same as the first waxy phase in some embodiments. As in step S9, a second volatile phase that includes a second compound to be sequestered is prepared. The second compound may be distinct from the first compound, or, in some embodiments, may be the same compound as the first compound in a different concentration. As in step S10, a second emulsion is created from the second waxy phase and the second volatile phase. As in step S11, the second emulsion may be deposited on card 415. The second emulsion may be deposited as, for example droplets or as a layer 218. Droplets may be applied directly opposite from or directly on top of heat receiving elements 412. A second emulsion layer 418 of may be deposited on top of or side-by-side with first emulsion layer 417. As in step S12, the second emulsion is cooled. Steps S8-S12 may occur in parallel with steps S3-S7.

Finally, as in step S13, the deposited emulsion(s) may be washed with a solvent to remove any volatile phase components that may have escaped the encapsulant 414 during manufacture. In some embodiments, the solvent may comprise one or more alcohols.

Referring back to FIG. 4, electronic monitors 100 may permit high-resolution and reliable data to be collected on the experimental animals while substantially avoiding inconsistent perturbations of the animals or cross-contamination between animals. And, electronic monitors 100 may be able to provide these advantages without substantially interfering with other aspects of conventional animal husbandry workflows. Electronic monitors 100 may thus be incorporated into an existing animal husbandry workflow without requiring revamping of various aspects of the workflow, such as technician training and existing equipment.

Electronic monitor 100 may include one or more atmospheric sensors 240 to detect one or more atmospheric conditions inside cage 110. Sensors 240 may include, for example, a humidity sensor to detect water vapor. The humidity sensor can be used, for example, to detect whether the cage has undesirably flooded with water or another liquid. Sensors 240 may also include sensors to detect percentage levels of various gases. For example, sensors 240 may include an ammonia sensor to detect a level of ammonia ($NH_3$) in the atmosphere of cage 110. A level of ammonia that is above a particular level may indicate an undesirably high level of waste of the experimental animals, for example, and therefore a desirability of replacing the flooring or bedding, moving the animals to another cage, or cleaning the cage. Sensors 240 may additionally include a carbon monoxide sensor to detect a level of carbon monoxide (CO) in the cage, a nitrogen dioxide sensor to detect a level of nitrogen dioxide ($NO_2$) in the cage, one or more sensors for a preselected group of oxidizing gases, and/or one or more sensors for a preselected group of reducing gases. Furthermore, sensors 240 may include a temperature sensor to detect a temperature inside the cage. Atmospheric sensors 240 may be disposed in contact with air coming out of cage 110, such as in the path of the air outlet, to avoid contamination of the inside of cage 110 while obtaining a desirably accurate reading of current atmospheric conditions inside cage 110.

The electronic components of electronic monitor 100 may also include one or more electromagnetic detectors 250, such as shown in the example of FIG. 4. Detectors 250 may be coupled to housing 120 at predefined positions. For example, these predefined positions may have a line-of-sight through one or more signal-interface sections 260 and into living space 145 of cage 110 when electronic monitor 100 is coupled to cage 110. The "line-of-sight" refers to a possible path of propagation of electromagnetic radiation that is suitably transparent for detection of the electromagnetic radiation by detectors 250. The path of propagation may either form a substantially straight line or change direction one or more times (the latter type being referred to here as an "indirect" line-of-sight). Electromagnetic detector 250 may thereby be adapted to detect electromagnetic radiation that is transmitted through signal-interface sections 260. In one example, one or more of electromagnetic detectors 250 has an indirect line-of-slight through section-interface section 260 into living space 145 of cage 110, such as shown in the example of FIG. 4. Furthermore, if housing 120 has a substantially airtight enclosure, the substantially airtight enclosure may be designed to contain electromagnetic detectors 250 therein to protect electromagnetic detectors 250 from dirtying or damage by the outside environment.

The electromagnetic detectors of the electronic monitor may include one or more cameras. The cameras may be able to capture video or, in other cases, still images. The optics of the cameras may be, for example, conventional camera optics, light-field camera optics, or structure-of-light camera optics. Furthermore, the cameras may be adapted to capture images in any suitable range of wavelengths, such as, for example, the visible spectrum, near infrared range, or far infrared range. For example, a camera may be adapted to detect radiation in the far infrared range to generate a signal that electronic monitor 100 uses to determine temperatures in cage 110.

The camera may be adapted to capture multiple different images of the space inside the cage, such as substantially the same area inside the cage, which can be processed together to enhance the data richness, such as the image resolution, of the observed area. For example, two or more such images may be digitally processed to deconvolve scratches and/or other imperfections in the transparency of the cage from the image. In one exemplary embodiment, the camera is adapted to be repeatedly physically shifted between at least two predefined positions in order to capture respective images from at least two different perspectives. Alternatively, the camera could be held still while a mirror or other optical device is physically shifted between at least two predefined positions in order to capture the images from the two or more optical perspectives. Alternatively or in addition, the camera may be a light-field camera that is adapted to capture two or more images simultaneously at different focus levels. In yet another embodiment, two or more fixed cameras may be positioned next to each other to simultaneously capture two or more images of substantially the same area from slightly different perspectives.

Electronic monitor 100 may also have one or more electromagnetic sources 270, which may be coupled to housing 120 at a predefined position that has a line-of-sight into living space 145 of cage 110, such as through signal-interface section 260. Sources 270 may be adapted, in one embodiment, to illuminate one or more desired areas of living space 145 to enhance detection by electromagnetic detectors 250. For example, one of sources 270 may illuminate an area of living space 145 with light at one or more wavelengths that are selected to reduce or minimize perturbation of experimental animals 235, and the illuminated area of living space 145 may be observed via one of electromagnetic detectors 250 that is adapted to detect light at those preselected wavelengths.

Housing 120 of electronic monitor 100 may have a substantially flat wall of one of walls 140 that is adapted to, when electronic monitor 100 is coupled to cage 110, be positioned approximately adjacent to signal-interface section 260 of cage 110. For example, if cage 110 is mounted directly underneath electronic monitor 100, such as shown in the examples of FIGS. 1A, 1B, and 3, then signal-interface section 260 may be located in a top wall of cage 110. In one version, cage 110 is disposable between cycles of housing a set of experimental animals. In one version, signal-interface section 260 may be any substantially transparent area of walls 140 of cage 110.

Electronic monitor 100 may further include one or more acoustic sensors 280, such as microphones, to capture sounds from inside cage 110. Acoustic sensors 280 may be adapted to capture sounds in any suitable range of frequencies, such as, for example, in an infrasonic, human-audible, or ultrasonic range. Acoustic sensors 280 may be adapted to capture sounds in the range of from about 0 Hz to about 100 kHz. In one example, acoustic sensors 280 may be adapted to capture sounds in the range of from about 15 kHz to about 35 kHz to listen to mouse vocalizations. In another example, acoustic sensors 280 may be adapted to listen for predefined distinctive sounds made by experimental animals under known conditions. For example, a controller 320 may analyze recordings of mouse vocalizations to characterize to the vocalization call as, for example, mating calls, exploration calls, or distress calls. For example, as understood by those of skill in the art, rodent vocalizations can be characterized into sets of syllables of waveform patterns (including short, flat, one frequency jump, multiple frequency jump, U-shaped, modulated, composite, upward, and downward waveforms). Certain patterns of such syllables and intervals between them may be indicative of rodent mating calls in particular contexts. Rodent vocalization analysis techniques are described in Chabout et al. "Adult Male Mice Emit Context-Specific Ultrasonic Vocalizations That Are Modulated by Prior Isolation or Group Rearing Environment." *PLoS ONE* 7(1). 2012 and Chabout et al. "Male Mice Song Syntax Depends on Social Contexts and Influences Female Preferences." *Frontiers in Behavioral Neuroscience*. Vol. 9, No. 76, 2015, both of which are incorporated herein by reference in their entirety.

Furthermore, electronic monitor 100 may have acoustic emitters 290 to transmit sounds into cage 110. In one version, acoustic emitters 290 transmit one or more sounds into living space 145 that are stimuli to observe a response, or obtain a predicted response, from the experimental animals. These acoustic stimuli may be part of the overall experiment being performed on the animals, for example. The acoustic stimuli may, for example, simulate noises created by the same type of experimental animals or predators of the experimental animal. Alternatively or in addition, acoustic emitters 290 may be used in a noise-canceling mode to substantially cancel out unwanted noises created in the environment outside cage 110. These may include, for example, loud or sudden noises by nearby laboratory staff, equipment, or animals in other cages that may otherwise perturb the experimental animals.

In one version, a weight scale 300 is provided inside the cage to measure the mass of an experimental animal. Weight scale 300 may transmit the measured mass data to electronic monitor 100 by electromagnetic transmission that does not substantially affect the sterility barrier between living space 145 in cage 110 and electronic monitor 100. For example, weight scale 300 may transmit the measured mass information to electronic monitor 100 by a modulated near-infrared beam or radio frequency (RF) signal. Weight scale 300 may be located in living space 145 where an experimental animal can identifiably or predictably stand on scale 300.

Electronic monitor 100 may also include one or more user interfaces 310 to display information to a human supervisor or receive one or more inputs from the human supervisor. The human supervisor may be, for example, an animal-husbandry technician who is responsible for the physiological and psychological condition of the animals, a scientist who is conducting the experiment on the animals, or another kind of human analyst. One or more of user interfaces 310 may be adapted to display a compilation of information received from electronic monitors 100 at individual housings 110 of electronic monitors 100, at the level of the rack (such as rack 230 shown in FIG. 3), or at client devices such as personal computers or handheld devices. The compilation may be, for example, a summary or parallelized display of information derived from electronic monitors 100. The presented information may include one or more of raw data from ambient sensors 130 of electronic monitors 100, raw data from atmospheric sensors 240, raw data from electromagnetic detectors 250, raw data from acoustic sensors 280, raw data from weight scales 300 inside cages 110, and information resulting from processing of such raw data by one or more of controllers 320. For example, user interfaces 310 may be adapted to display a plurality of metrics to the human supervisor as a guide, receive an input relating to one or more of the metrics from the human supervisor, and navigate through raw data associated with the metrics based on the human input. For example, the human input may be associated with a status of experimental animals 235.

Certain user interfaces 310a may be disposed on housing 120 of electronic monitor 100 itself, or, additionally or alternatively, at one or more remote locations. User interfaces 310 may include, for example, one or more light-emitting diodes (LEDs) (such as shown in FIG. 4 by user interface 310a), two-dimensional color displays, or acoustic speakers.

Electronic monitors 100 may also include at least one controller 320 to control the operation of electronic monitors 100, compound releasing system 400, control user interfaces 310 to interface with a human supervisor, and/or interface with an external server or network. Controller 320 may automatically control one or more aspects of operation of electronic monitor 100 and/or compound releasing system 400, and may be adapted to largely or wholly automate the operation of electronic monitor 100 and/or compound releasing system 400. The controller may, for example, receive inputs from a human user, provide instructions to other components of monitor 100, perform processing of data received from ambient sensors 130, atmospheric sensors 240, electromagnetic detectors 250, camera 444 of compound releasing system 400, acoustic sensors 280, and weight scale 300, and/or output signals, such as alerts or other indicators. Controller 320 may be adapted, for example, to receive signals from ambient sensors 130, atmospheric sensors 240, camera 444, electromagnetic detectors 250, acoustic sensors 280, and weight scale 300; to transmit control signals to electromagnetic sources 270 to provide electromagnetic radiation into living space 145; to transmit signals to acoustic emitters 290; to transmit signals to user interfaces 310; or transmit and receive signals to compound releasing 400 and its components.

Controller 320 may include one or more microprocessors, controllers, processing systems, computers, and/or circuitry, such as any combination of hardware or software modules. Components of the controller may be distributed across one or more different physical locations and these components may communicate with each other to perform the operations of the controller. For example, components of controller 320 may be physically located at the individual electronic monitors 100, such as at the level of rack 230 (e.g., connected to rack-level data input and output ports), and/or at remote client devices such as personal computers or handheld devices.

Controller 320 may be implemented in any quantity of hardware components, such as including Raspberry Pi, an integrated circuit such as, for example, an application-specific integrated circuit (ASIC), field-programmable gate array (FPGA), or "system on a chip" (SoC), and/or other processor, memory, bus, input/output, or communications systems. Furthermore, some or all of these hardware components may be located locally or remotely. For example, controller 320 may be implemented partially or entirely through cloud computing. Controller 320 may operate any commercially available operating system software, including, for example, Linux, Windows, MacOS, iOS, Android, Unix, OS/2, or any other commercially available and/or custom software. For example, controller 320 may operate customized animal-monitoring and signal-processing software. Furthermore, controller 320 may include one or more types of input devices, such as for example a touchpad, keyboard, button panel, mouse, microphone, or voice recognition device.

Controller 320 may be adapted to process received data and/or human inputs to determine values of one or more metrics relating to experimental animals 235 or living space 145. The metrics may include one or more physiological, behavioral, or environmental metrics. Physiological metrics may include, for example, respiration rate, health check, heart rate, body weight, thinness, body temperature, metabolism, coat characteristics such as rough hair coat, stress level, a Body Condition Score ("BCS"), alopecia, whether the animal is dead, ataxia or another central nervous system (CNS) disorder, circling or head tilt, dehydration, dermatitis, distended abdomen, dyspnea, dystocia, ear problems, emaciation, eye problems, fight wounds, hunched posture, hydrocephalus, irregular gait, lesions, lethargy, listlessness, malocclusion, necropsy, the number of animals in a cage, paleness of color, the presence of post-operative staples, prolapse, pruritus, seizure, other sickness, or the presence of a tumor. Examples of measuring the physiological metric of respiration rate are described in U.S. patent application Ser. No. 14/788,749 to Heath et al., which is incorporated herein by reference in its entirety. Behavioral metrics may include, for example, activity states and patterns, food and water consumption by the experimental animals, whether an animal appears to be missing from a particular region or the entire cage, a sleep or awake state, an animal biting itself, an animal biting its tail, a caught or trapped state of an animal, contact between animals, defecation, urination, drinking, eating, exercise, foraging, grooming, a hunched posture, inactivity, nose-poking, rearing up, running, repetitive behavior, licking, scratching, fighting, wincing, exploring behavior, hiding behavior, fear behavior, mating behavior, animal location in cage over time, animal locomotion within particular areas of the cage, and sociability. Environmental metrics may include, for example, an amount of water or food remaining for consumption by the animals in a cage, high or low humidity, high or low ammonia level, high or low environmental temperature, illumination level, an ajar state or equipment, a broken state of equipment, a slotted or unslotted state of the cage, an open state of the cage, a change in bedding, a fill-up of food or water, maximum or minimum humidity for a rack containing the cage, maximum or minimum temperature for a rack containing the cage, a scent or other compound released into the atmosphere of the cage, and general cage or rack problems.

Controller 320 may present one or more of the monitored metrics on one or more of user interfaces 310 for observation by a human supervisor. In one version, the monitored metrics are displayed to the human supervisor in a "fused" manner. This means that the monitored metrics are displayed or otherwise presented to the human supervisor in a compact or ergonomic manner that overlays, joins, or compares a plurality of metrics that are being, or have been, monitored. For example, temperatures or measurements of activity in different cages may be overlapped in the same plot for ready visual comparison by the human supervisor. This may allow the human supervisor to efficiently or ergonomically observe the conditions in different cages, or evaluate the conditions in a particular cage of interest relative to other cages.

Multiple animals that are under the same experimental conditions may be selected to be housed in the same cage. For example, animals in a control group may be housed together, while animals in a particular experimental group may be housed together. When animals that are under the same experimental conditions are housed in the same cage, it may not be necessary for electronic monitor 100 to track the individual identities of the animals. Rather, since the mice may be treated as experimentally identical, aggregated or averaged information relating to all of the mice in a particular cage may suffice for purposes of the experiment.

Controller 320 may be adapted to process one or more input signals received from the human supervisor through one or more of user interfaces 310 as inputs to a machine learning algorithm that is executed by controller 320. For example, controller 320 may display to the human supervisor, via one of user interfaces 310, a condition inside the cage, such as a predicted status of an experimental animal. This may be referred to as a "state signal." The predicted status of an experimental animal may be, in one example, that the animal is healthy or sick. Controller 320 may simultaneously display a level of confidence that controller 320 has in its prediction or estimation of the condition. The human supervisor may observe the experimental animal, either remotely through the user interface or in person, and confirm or reject the prediction. Alternatively or in addition to confirmations and rejections, the human supervisor may provide feedback by setting parameters under which controller 320 predicts the condition. Based on this repeated feedback from the human supervisor, controller 320 may automatically learn to associate a received signal with a particular condition.

In addition to obviating direct, physical human interaction, electronic monitors 100 can couple to cages 110 in a manner that does not otherwise interfere with the experimental animals. For example, electronic monitors 100 may obviate a need to surgically implant or otherwise insert any sensor, needle, or other device into the body of an experimental animal or to tether the experimental animal in any way. Furthermore, by coupling to cages 110 that are substantially closed from all sides, electronic monitors 100 may be capable of handling husbandry and experimental tasks without placing detectors 250 or sensors 280 in contact with the atmosphere of the living space 145 of the experimental animals.

Controller 320 may control electromagnetic detectors 250, and optionally also electromagnetic sources 270, to determine, e.g., the locomotion and position of one or more of the experimental animals by optical methods. These optical methods and devices may also be substantially insusceptible to acoustic conditions inside or outside of the cage. Electromagnetic detectors 250 and/or electromagnetic sources 270 may be used to observe the experimental animals using light in the visual spectrum in one version. In another version, however, electromagnetic detectors 250 and/or electromagnetic sources 270 may use infrared light or one or more wavelengths of light that are substantially invisible to the experimental animals. For example, in one embodiment electromagnetic detectors 250 may detect ambient light in the visual spectrum during daytime hours and invisible light such as in the infrared spectrum during nighttime hours. These wavelengths of light used may be selected in part based on the normal behavioral characteristics of the animals, such as whether the experimental animals are diurnal or nocturnal.

Controller 320 may receive a time sequence of images (which can be referred to as "frames" of a video) of an experimental animal from electromagnetic detectors 250. The images may be of a resolution that is selected to be suitably high that changes in the image corresponding to respiration of the experimental animal are detectable. In one example embodiment, each of the images is a two-dimensional color image. Controller 320 may apply one or more calibrations or corrections to the image, such as for example a geometric camera calibration to correct lens distortion.

Controller 320 can process the video from electromagnetic detectors 250 to identify the positions of and the movement of experimental animals. In one version, images from multiple electromagnetic detectors 250 corresponding to different perspectives into the living space of the experimental animals are synthesized to generate a single image with better visibility of the experimental animals, such as the entire cage floor that can be traversed by the animals. For example, these multiple images may have been captured at substantially the same point in time to generate a synthesized image for that time point. The synthesized images may then form a synthesized video composed of a time sequence of the synthesized images as frames. This may avoid occlusions that are not present from one or more of the detector perspectives and improve the accuracy of imaging.

Controller 320 may use a homography to project the images onto a plane corresponding to the cage floor as part of generating the synthesized image. For example, the projected views may be fused into a synthetic overhead view of the cage floor, where the electromagnetic detector (e.g., camera) chosen for certain pixel information in the synthetic view is selected to reduce occlusions and maximize sensing resolution. Generating a synthesized image may facilitate setting parameters in terms of physically meaningful or intuitive dimensions.

Figure 6A:
FIGS. 6A and 6B are example of embodiments of grayscale images of two separate mice in the same cage taken by different respective cameras from different respective viewpoints.
Figure 6B:
Figure 7A:
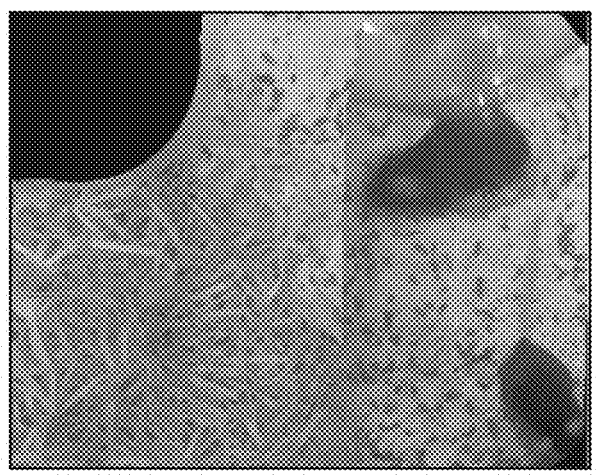
FIG. 7A is a grayscale image that has been generated by synthesizing two images of the mice in FIGS. 6A and 6B from the respective cameras used to capture the images of those figures.

FIGS. 6A and 6B are example of embodiments of grayscale images of two separate mice in the same cage taken by different respective cameras from different respective viewpoints. As shown in 6B, the living space may include a perceived protected area or hiding place for an experimental animal such as hutch 481. FIG. 7A is a grayscale image that has been generated by synthesizing two images of the mice in FIGS. 6A and 6B from the respective cameras used to capture the images of those figures.

The video frames—whether synthesized or otherwise—may be divided into a tessellation of geometric boundaries that define cells. The tessellation may be a rectilinear grid, for example. Displacements of the cells between sampling times can then be evaluated to determine which displacements correspond to movements and positions of an experimental animal.

The dimensions and shapes of the cells may be preselected to optimize discrimination of cell displacement (i.e., tracking of a cell across a displacement during a time interval) although the pixel intensities within the displaced cell can change slightly as a result of the movement. In one version, the cells are defined to have a size of from about 0.001 cm$^2$ to about 400 cm$^2$. In one example, the cells are defined to have a size of from about 0.25 cm$^2$ to about 4 cm$^2$, such as for a mouse or other small rodent.

Controller 320 may process magnitudes and directions of displacements of the cells between sampling times to determine an optical flow of the video signal and output an optical-flow signal that encodes the computed or estimated optical flow. The optical flow may be a representation of movement of patterns in a video between one image frame and another image frame. The optical flow may be described, for example, as a vector field composed of vectors, each vector having a magnitude component and a direction component.

In one embodiment, the vector field representing displacements for each grid cell is encoded by two two-dimensional matrices of floating-point numbers. The optical flow is the displacement of the content of a grid cell between a first time (t_0) and a second time (t_1). The optical flow may be determined by matching the displacement of each of the cells to another set of pixels that is believed to track the physical movement of the feature that was imaged in that cell. In one example, the matching set of pixels is a nearby set of pixels that has the same size as the cell. This matching may be performed at the pixel resolution of the underlying image.

In one embodiment, a correlation method is used for estimating optical flow in which a cell at the first time (t_0) is cross-correlated to its best matching displacement in the two-dimensional image at the second time (t_1) within a predefined search window. However, other suitable matching algorithms may be used. For example, other methods of estimating optical flow include differential methods and energy-based, phase-based, and other region-based techniques.

The matrix pairs may encode the vector field in polar coordinates, where the first matrix encodes a magnitude component of each vector in the vector field while the second matrix encodes a direction component for that vector (e.g., as an angle). Alternatively, the first and second matrices may encode orthogonal components of each vector of the vector field in Cartesian coordinates (i.e., "x" and "y" coordinates).

Figure 7B:
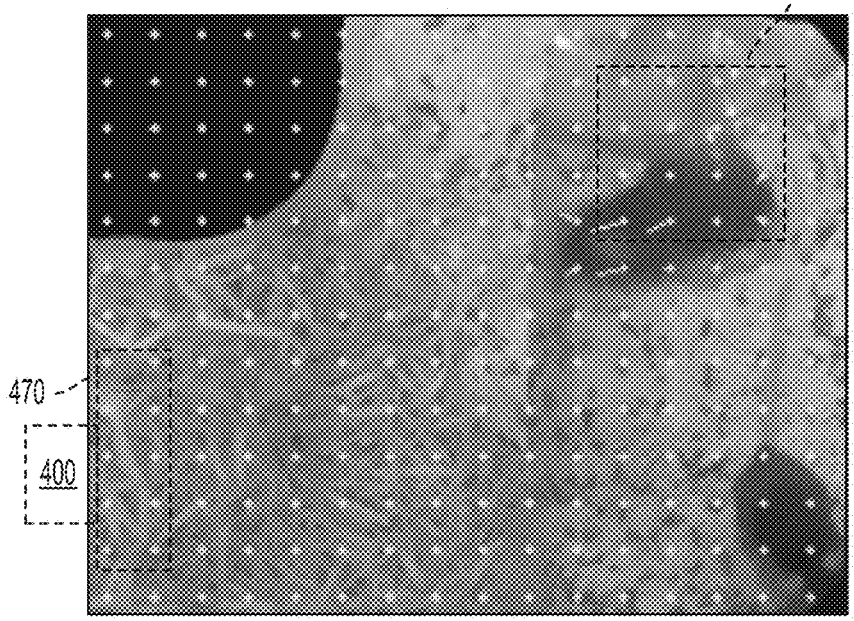
FIG. 7B is the grayscale image of FIG. 7A with an example of an embodiment of a vector field representing optical flow overlaid on the image.
Figure 8:
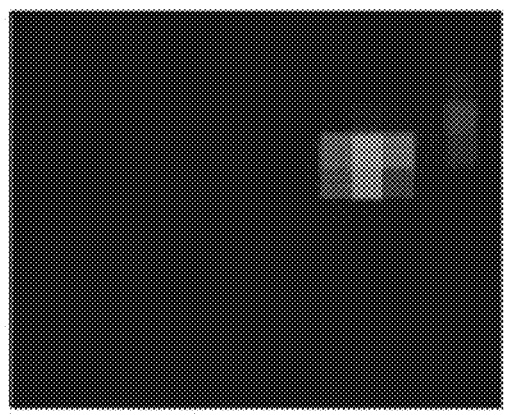
FIG. 8 is a pixelated representation of the magnitude component of the vector field shown in FIG. 7B across differential spatial cells.

FIG. 7B is the grayscale image of FIG. 7A with an example of an embodiment of a vector field representing optical flow overlaid on the image. FIG. 7B also illustrates a hiding area 480 corresponding to the position of hutch 281 and a scent area 470, which may be adjacent to the location of a compound releasing system 400 that releases scents with a distinct locus. Other hiding areas 480 may also include corners of the cage or other small, protected enclosures. FIG. 8 is a pixelated representation of the magnitude component of the vector field shown in FIG. 7B across differential spatial cells. The vector field of FIG. 7B and corresponding pixelated data of FIG. 8 illustrate the position and movement of an animal moving in hiding area 480. Thus, this data may indicate that the animal is exhibiting hiding behaviors.

Figure 9:
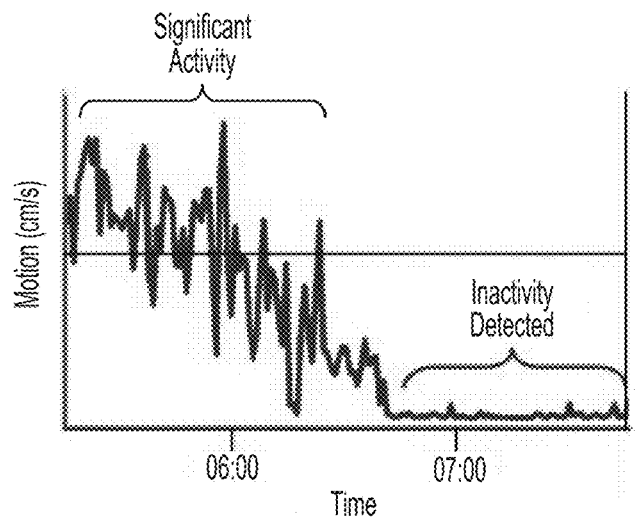
FIG. 9 is a plot of an example of an embodiment of a magnitude of motion in an optical flow over time.

FIG. 9 is a plot of an example of an embodiment of a magnitude of motion in an optical flow over time. Such a plot may depict magnitude of motion in an optical flow over time in a particular area or areas. By using thresholds of motion, such data may be used to identify periods of significant activity and periods of inactivity. For example, if FIG. 9 represents movement within scent area 470 immediately after compound releasing system 400 releases a scent of interest to the animal, for example, that of food or female rodent urine, the initial period of significant activity may indicate that the animal is displaying exploring behavior. That is, the animal may be moving in and around scent area 470 to try to determine the source of the scent. The end of the period of significant activity and/or the beginning of the period of inactivity may indicate when the animal has abandoned its exploring behavior. The duration of the exploring behavior may be used to characterize the animal's response to the scent.

Exploring behavior may also be characterized by significant activity in the entire living space, rather than merely a selected area or areas. Measuring locomotion across the entire living space may be more appropriate in situations where a released odor is not dispersed from a distinct locus from the animal's perspective, for example when odors may be released from an air supply pod 450.

In another example, if FIG. 9 represents movement within the entire living area where compound releasing system 400 releases a scent of a predator at a time of approximately 06:30, the detection of inactivity soon after the scent is released may indicate that the animal is displaying hiding behavior. That is, the animal may have quickly found a place to hide and ceased locomoting.

Figure 10:
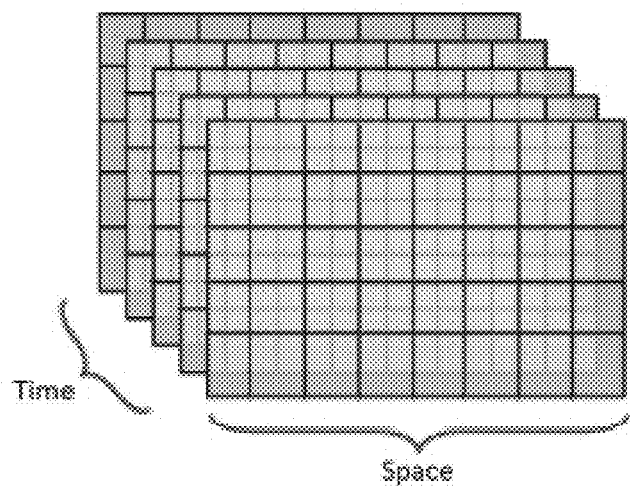
FIG. 10 is a schematic illustration of an example of an embodiment of cells of an image in time and two-dimensional space dimensions.

FIG. 10 is a schematic illustration of an example of an embodiment of cells of an image in time and two-dimensional space dimensions. It may represent a space-time volume of motion detection arrays. Controller 320 may process the optical flow (e.g., between the time planes in FIG. 10) to determine a spatial region of interest (ROI). In one version, controller 320 evaluates the optical flow within a particular temporal ROI to determine, within that temporal ROI, a spatial ROI.

Figure 11:
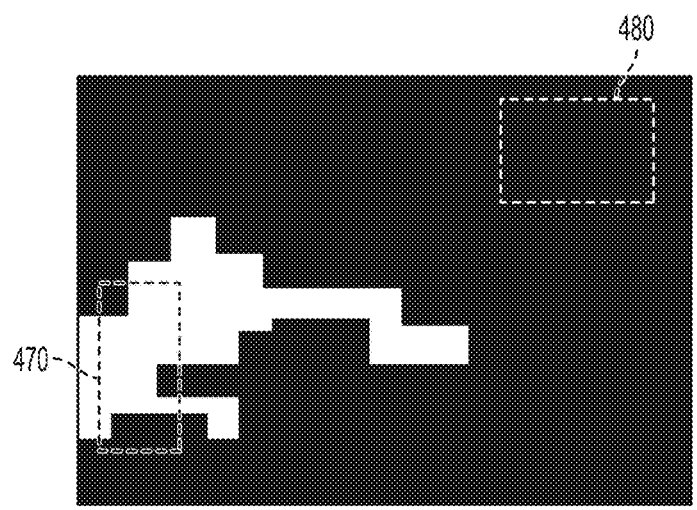
FIG. 11 is a plot of an example of an embodiment of a position of a locomoting experimental animal over time.

FIG. 11 may represent an example of a pixelated representation of a spatial ROI during a particular temporal ROI. It may show a position of a locomoting experimental animal over time. The temporal ROI may be selected based on when a stimulus is given to an animal. As an illustration, the temporal ROI may be a one minute period after a scent is released by compound releasing system 400 and the white pixels may represent an animal's spatial ROI. Each white pixel of FIG. 11 may represent a location where at least one time plane had a motion vector exceeding a threshold magnitude during the temporal ROI. In this illustration, this evaluation of space-time volume data may suggest exploring behavior. That is, the spatial ROI may depict experimental animal movement towards, in, and around scent area 470 during a temporal ROI after scent dispersal.

In other embodiments, a pixelated representation of a spatial ROI during a particular temporal ROI may also be generated without optical flow analysis by using computer vision techniques to determine the position of an animal. For example, the video signal can be evaluated using animal head detection algorithms on each video frame to determine animal positions. In another example, experimental animals may have tattooed tails, which may be identified within frames of the video signal to determine animal positions. Such positions in the video frames may be aggregated across the temporal ROI to generate an image similar to FIG. 11.

Behaviors, such as exploring and hiding behaviors, may be characterized by, for example, duration and/or intensity. For example, an exploring behavior may be quantified by the amount of time that an animal remains in a target area(s); by the amount of time an animal exhibits a certain level of movement in response to a stimulus either in a target area(s) or in the entire living space; by the speed of an animal's movement within a target area and/or during a temporal ROI; and/or by the size of the footprint of an animal's movement or position within a target area(s) or the entire living area during a temporal ROI. Similarly, a hiding behavior or fear response may be quantified by the amount of time that an animal remains in a target area(s) and/or by the amount of time an animal exhibits a certain level of inactivity in response to a stimulus.

Figure 12:
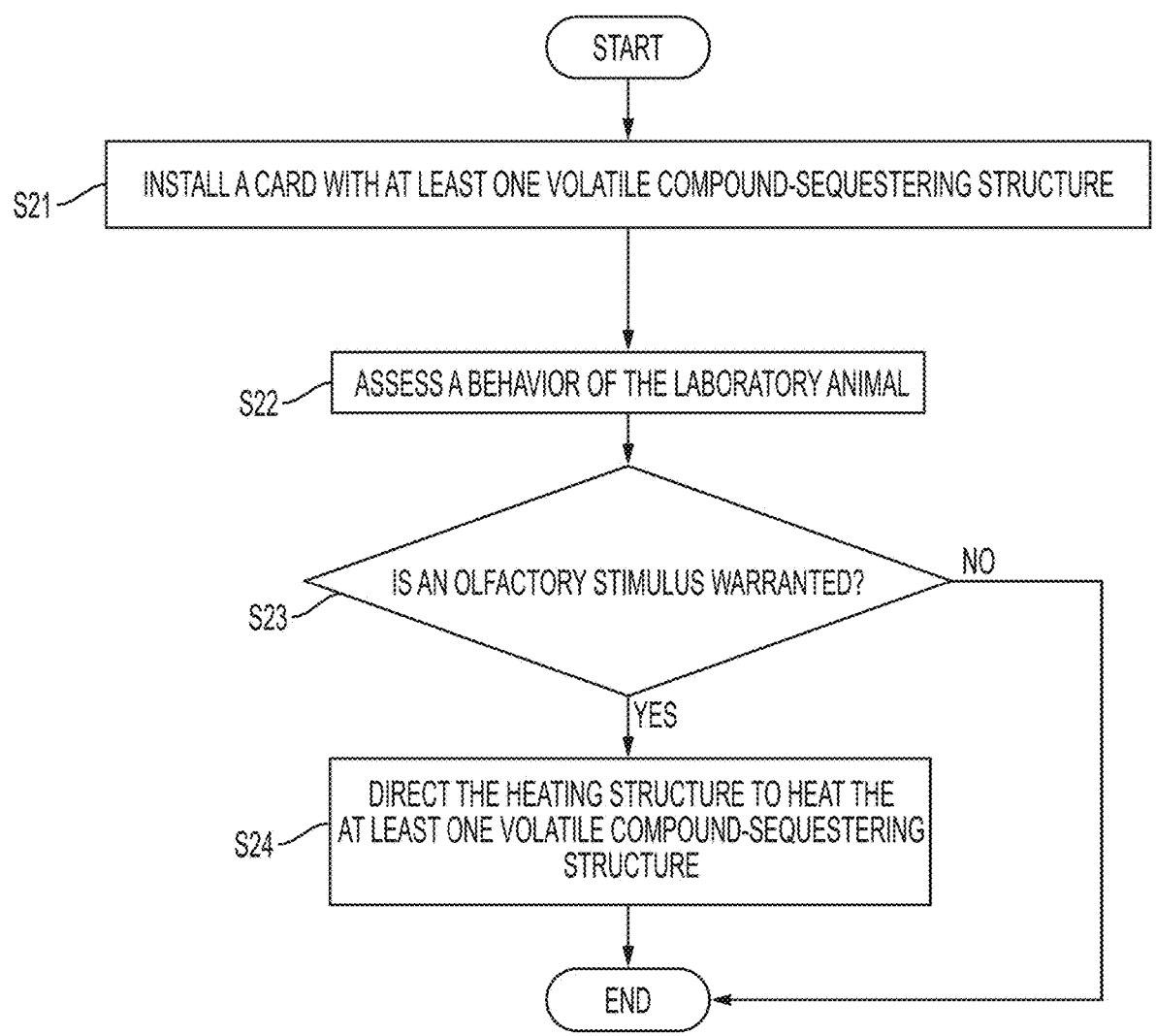
FIG. 12 is a flowchart of an example of an embodiment of a process of delivering an olfactory stimulus to an experimental animal in a cage.

FIG. 12 is a flowchart of an example of an embodiment of a process of delivering an olfactory stimulus to an experimental animal in a cage. Such a cage may include a heating structure and a card-receiving element. Depending on the objectives and limitations of animal research being conducted, some steps may be omitted, altered, or reordered. As in step S21, a card apparatus 410 with at least one volatile compound-sequestering structure is installed.

As in step S22, a behavior of the animal is assessed. The behavior may be assessed manually. For example, a human observer may assess whether or not the animal has completed a certain task and is deserving of a reward. Or, the behavior may be assessed automatically via controller 320 (or 320a). For example, whether and to what degree the experimental animal is exhibiting exploring behavior, hiding behavior, a certain level of locomotion activity, inactivity, a fear response, mating behavior, and/or any other detectable behavior(s) may be assessed. In another example, the position of the animal in a cage may be assessed. The animal research protocols may, for example, call for the release of a particular food scent if a hiding behavior is exhibited. In some embodiments, the assessment may pertain to one or more physiological or environmental metrics instead of, or in addition to, a behavioral metric(s).

The behavior may be automatically assessed by generating a video signal with an optical detector(s), processing the video signal to generate an optical flow signal, and analyzing the optical flow signal to determine if a behavior warranting an olfactory stimulus exhibited. Alternatively or additionally, the behavior may be assessed by generating an audio signal with an acoustic sensor(s) and processing the audio signal to determine if a behavior warranting an olfactory stimulus is exhibited.

As in step S23, if it is determined based on the assessment that an olfactory stimulus is not warranted, for example, based on a clinical protocol, the method is completed. If it is determined based on the assessment that an olfactory stimulus is warranted, the method proceeds to step S24. Step S23 may be carried out by controller 320e (or 320) automatically based on programming, or manually based on input from a human observer.

As in step S24, an olfactory stimulus may be provided to the animal via compound releasing system 400. Controller 320e may direct heating structure 440 to heat the at least one compound-sequestering structure 411 to a specified temperature for a specified duration in order to release an olfactory stimulus into the living space. In certain embodiments, another stimulus, for example, an electric shock or food treat may be delivered to the animal concurrently with the olfactory stimulus. The above-described process, or a portion thereof, may be repeated based on the objectives and limitations of the animal research being conducted.

In some embodiments, the determination of whether an olfactory stimulus is warranted may be based on a research protocol or another different criteria that is not based on an assessment one or more physiological, environmental, and/or or behavioral metric(s). In such embodiments, step S22 may proceed after steps S23 and S24.

A cognitive state of an experimental animal may be assessed using an olfactory habituation/dishabituation test. By comparing an animal's response to a first novel olfactory stimulus to the animal's response to a repeated exposure to that same first olfactory stimulus, it may be assessed whether the animal habituates to the scent (e.g., has a decreased response), which may be indicative of high cognition, or does not habituate, which may be indicative of lower or lost cognition or repetitive interest. Then, by comparing an animal's response to a second novel olfactory stimulus after repeated exposure to that first, familiar olfactory stimulus, it may be further assessed whether the animal is dishabituated to the second olfactory stimulus (e.g., has a increased response compared with the response from the second presentation of the first olfactory stimulus and/or a response similar to that of the first presentation of the first olfactory stimulus), which may be a further indication of high cognition, or shows no increased interest in the second olfactory stimulus as compared to the second presentation of the first olfactory stimulus, which may be a further indication of lower or lost cognition. Additional description of an olfactory habituation/dishabituation test is provided in M. Yang & J. Crawley. "Simple Behavioral Assessment of Mouse Olfaction." *Curr. Protoc. Neurosci.* July 2009, and M. Tong et al. "Properties and Mechanisms of Olfactory Learning and Memory." *Frontiers in Behavioral Neuroscience*. Vol. 8, No. 238, 2014, which are incorporated herein by reference. Depending on the objectives or limitations of animal research being conducted, some steps may be omitted, altered, or reordered.

Figure 13:
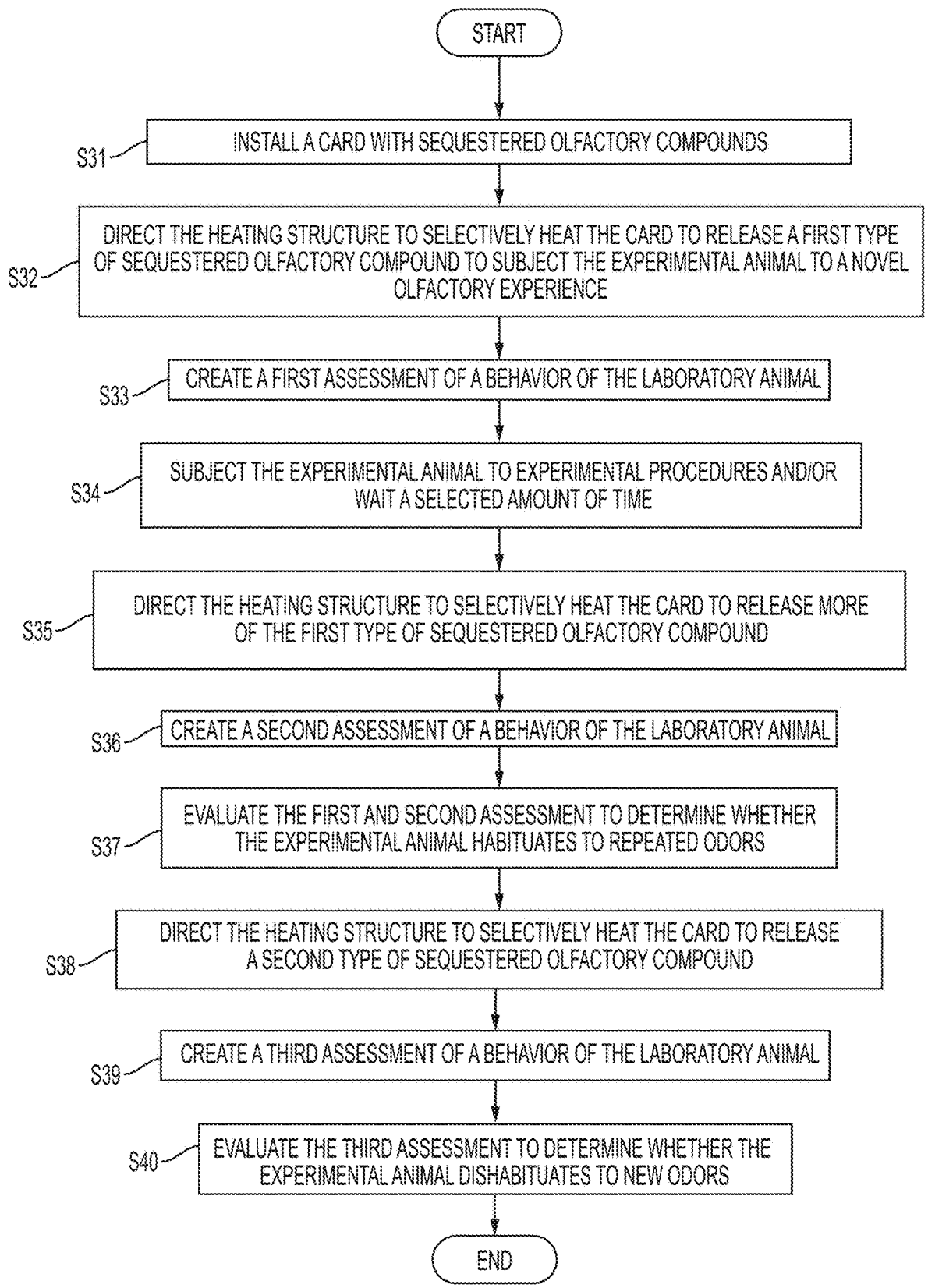
FIG. 13 is a flowchart of an example of an embodiment of a process of testing habituation/dishabituation in an experimental animal in a cage.

FIG. 13 is a flowchart of an example of an embodiment of a process of testing habituation/dishabituation in an experimental animal in a cage. Such a cage may include a heating structure 440 and a card-receiving element 430. Depending on the objectives or limitations of animal research being conducted, some steps may be omitted or altered. As in step S311, a card apparatus 410 with sequestered olfactory compounds is installed.

As in step S32, a novel olfactory stimulus may be provided to the animal via compound releasing system 400. Controller 320e (or 320) may direct heating structure 440 to selectively heat the card to release the first type of sequestered first type of olfactory compound. The novel olfactory stimulus may be a reward smell. In some embodiments, the novel olfactory stimulus may be provided only when the experimental animal is in a specified location in the cage and/or when other physiological, environmental, and/or behavioral metric(s) are met.

As in step S33, the responsive behavior of the animal is assessed. The behavior may be assessed automatically via controller 320 (or 320a), or alternatively or additionally may be assessed manually via a human observer. An automatic behavioral assessment may be accomplished by processing video data generated by one or more optical detectors of the cage and/or by processing auditory data generated by one or more acoustic sensors of the cage.

As in step S34, the experimental animal may be subjected to experimental procedures and/or a specified duration of time may be allowed to pass. For example, a drug for which potential cognitive effects are being tested may be administered to the animal. In another example, 15 minutes are allowed to pass.

As in step S35, a second olfactory stimulus may be provided to the animal via compound releasing system 400. Controller 320e (or 320) may direct heating structure 440 to selectively heat the card to release more of the first type of sequestered olfactory compound. Compared to step S32, the first type of sequestered olfactory compound released in step S35 may be released in the same amounts/concentrations or in different amounts/concentrations. Because the same type of olfactory compound is released in steps S32 and S35, the second olfactory stimulus of step S35 is not novel to the experimental animal. In some embodiments, this repeated olfactory stimulus may be provided only when the experimental animal is in a specified location in the cage and/or when other physiological, environmental, and/or behavioral metric(s) are met.

As in step S36, the responsive behavior of the animal is assessed for a second time.

As in step S37, the first and second behavioral assessments may be evaluated to determine the cognitive state of the experimental animal, such as whether the experimental animal habituates to new odors. For example, if the novel scent was of potential interest to the experimental animal, for example, a new food smell such as peppermint, vanilla, almond, or banana extract, the first behavioral assessment may have indicated exploring behavior, or exploring behavior of a certain duration or intensity. If the animal habituated to the scent, for example, by remembering that it found no food as a result of its prior exploratory behavior, the second behavioral assessment may indicate substantially reduced or no exploratory behavior. Here, the evaluation may reveal no decrease in the cognitive state of the animal. If the animal did not habituate to the scent, for example, by failing to remember or forgetting that it found no food as a result of its prior exploratory behavior, the second behavioral assessment is likely to indicate exploratory behavior similar to that of the first. Here, the evaluation may reveal a decreased cognitive state.

Steps S38-S40 may be included to add robustness to the olfactory habituation/dishabituation test by evaluating whether an experimental animal may have habituated to multiple smells and not merely the scent of the tested first olfactory compound. This may be useful, for example, in determining whether the experimental procedure may have damaged an animal's ability to smell and that such damage, rather than a change in cognition, caused differences in the first and second behavioral assessments.

As in step S38, a second novel olfactory stimulus may be provided to the animal via compound releasing system 400. Controller 320e (or 320) may direct heating structure 440 to selectively heat the card to release a second type of sequestered olfactory compound to subject the experimental animal to a second novel olfactory experience.

As in step S39, the responsive behavior of the animal is assessed for a third time. Then, as in step S40, the third behavioral assessment is evaluated to determine whether the experimental animal dishabituates to new odors. Here, the third behavioral assessment may be compared to the first and/or second behavioral assessments.

In some embodiments, methods of testing habituation/dishabituation may use more types of olfactory compounds and more exposures to each compound type, for example when a research protocol calls for repeated or more thorough cognitive testing. For example, in one version, a habituation/dishabituation testing method may utilize up to six distinct olfactory compound types and up to three dispersements of each compound type.

Figure 15:
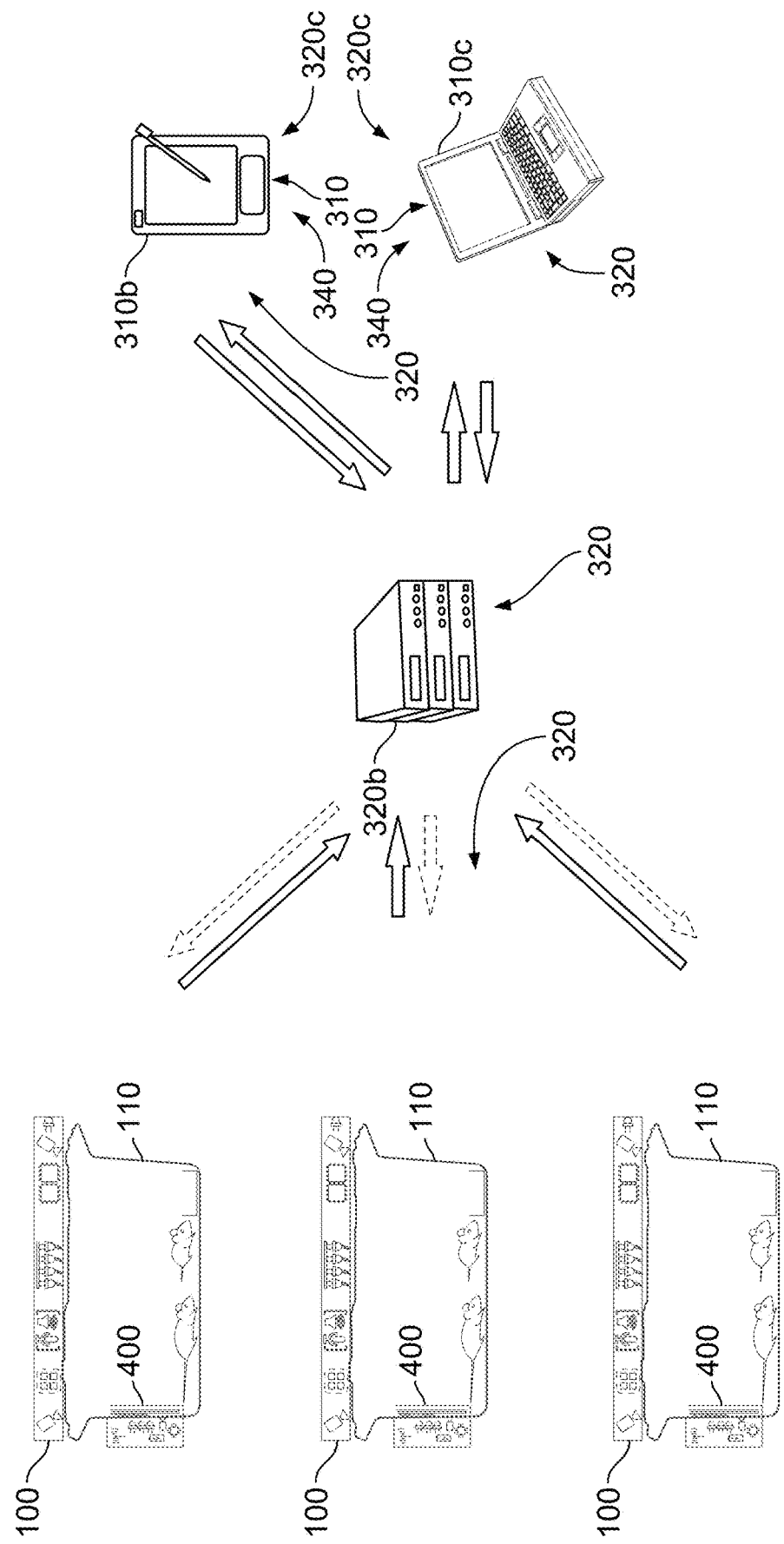
FIG. 15 is a schematic diagram of an example of an embodiment of multiple electronic monitors and compound releasing systems coupled to cages and interfaced with a human observer.

One or more of user interfaces 310 may be disposed at a location that is not mechanically attached to housing 120 of electronic monitor 100. FIG. 15 illustrates an example of an embodiment of multiple electronic monitors 100 and multiple compound releasing systems 400 respectively coupled to cages 110 and interfaced with a human observer. In this embodiment, arrayed electronic monitors 100 and compound releasing systems 400 communicate with an array controller 320b, such as a set of servers, that stores and processes the data from sensors 130, 240, 280, detectors 250, weight scales 300, controller 320a of electronic monitors 100, and/or controller 320e of compound releasing systems 400. Array controller 320b may serve, for example, a rack or multiple racks of electronic monitors 100 and compound releasing systems 400. Client devices 340 having user interfaces 310b,c, and controllers 320c which may be referred to as "client devices," may connect to array controller 320b. Client devices 340 may include, for example, personal computers (PCs), tablet computers, smartphones, or other suitable devices. The communication between client devices 340 and array controller 320b may be bidirectional, such as duplex. Client devices 340 may thereby control and/or request additional information from array controller 320b. Communication between electronic monitors 100 and compound releasing systems 400 and array controller 330 may be unidirectional from electronic monitors 100 to array controller 320b and compound releasing system controller 320e. Alternatively, however, this communication may be bidirectional, such as duplex. Client devices 340 or array controller 320b may thereby control and/or request additional information from electronic monitors 100 and compound releasing systems 400.

Returning to FIGS. 1A, 1B, 4, and 15 for the sake of exemplary illustration, the raw data from ambient sensors 130, atmospheric sensors 240, electromagnetic detectors 250, acoustic sensors 280, and/or weight scales 300 of electronic monitors 100 and/or camera 444 may be processed by controller 320 (which may include one or more of controller 320a, array controller 320b, controller 320c, and controller 320e) to condense the data into reduced-size data sets in one or more sequential stages corresponding to different locations. This may be desirable when there are practical limitations on data throughput. Condensing the data sets may refer to summarizing, compiling, compressing (by either lossy or lossless methods), and/or indexing the data sets. Condensing a video stream, for example, may involve decreasing frame rate or time-lapsing frames from the video stream, providing thumbnails of frames from the video stream, images that each represents a summed series of periodic exposures over time (such as to quickly visualize movement of the animals), or any other suitable method. In one example, a video stream can be compressed according to the H.264 video compression format. Condensing a numerical metric, such as respiration rate, temperature, humidity, or ammonia level, may involve, for example, decreasing resolution of the metric over time where the metric is in a predefined range that is considered normal or uninteresting, and increasing resolution of the metric where the metric is in a range that is deemed interesting.

Controller 320 (which may include one or more of controller 320a, array controller 320b, controller 320c, controller 320e, and servers 320d) may also cross-reference data sets from different metrics to improve the quality of the condensed data. In one version, data for one set of metrics is used to condense another metric. For example, if the first set of metrics is within an expected or otherwise "normal" range for a certain timespan, a video stream corresponding to the same timespan may be condensed or even eliminated for viewing at a downstream location. If, however, one of those metrics is outside of a normal range for a particular timespan, or if the set of metrics matches a predetermined trend or signature, a video stream corresponding to that timespan may be transmitted and/or stored in a less condensed form. The less condensed form may involve, for example, lossless compression as opposed to lossy compression, a higher resolution, or a higher frame rate.

Furthermore, controller 320 (or a human supervisor) receiving downstream data may instruct one or more of the ambient sensors 130, atmospheric sensors 240, electromagnetic detectors 250, acoustic sensors 280, camera 444, and/or weight scales 300 to actually generate higher-resolution raw data for a cage, time period, or physical area of one of cages 110 that is deemed unusually interesting. For example, controller 320 may determine that one of the metrics is currently outside of a normal range, or that a set of metrics are matching a predetermined trend or signature, and instruct one or more of the sensors or detectors described above to turn on or generate data at a higher resolution for a predefined time period. In one example, an anomalous metric may trigger controller 320 to turn on video cameras to record the experimental animals in a cage at high resolution and continuously for a predefined timespan.

Although the foregoing embodiments have been described in detail by way of illustration and example for purposes of clarity of understanding, it will be readily apparent to those of ordinary skill in the art in light of the description herein that certain changes and modifications may be made thereto without departing from the spirit or scope of the appended claims. It is also to be understood that the terminology used herein is for the purpose of describing particular aspects only, and is not intended to be limiting, since the scope of the present invention will be limited only by the appended claims.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of ordinary skill in the art upon reading this disclosure, each of the individual aspects described and illustrated herein has discrete components and features which may be readily separated from or combined with the features of any of the other several aspects without departing from the scope or spirit of the disclosure. Any recited method can be carried out in the order of events recited or in any other order that is logically possible. Accordingly, the preceding merely provides illustrative examples. It will be appreciated that those of ordinary skill in the art will be able to devise various arrangements which, although not explicitly described or shown herein, embody the principles of the disclosure and are included within its spirit and scope.

Furthermore, all examples and conditional language recited herein are principally intended to aid the reader in understanding the principles of the invention and the concepts contributed by the inventors to furthering the art, and are to be construed without limitation to such specifically recited examples and conditions. Moreover, all statements herein reciting principles and aspects of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary configurations shown and described herein.

In this specification, various preferred embodiments have been described with reference to the accompanying drawings. It will be apparent, however, that various other modifications and changes may be made thereto and additional embodiments may be implemented without departing from the broader scope of the claims that follow. The specification and drawings are accordingly to be regarded in an illustrative rather than restrictive sense.

We claim:

1. An apparatus for sequestering and releasing compounds into the air for laboratory animal experimentation, the apparatus comprising:
    a substantially flat card comprising a substrate with a first side and a second side, the substrate having a thermal conductivity of less than 1 W/m*K;
    a plurality of compound-sequestering structures affixed to the first side in a two-dimensional array; and
    a plurality of heat receiving elements that are affixed to the card and aligned behind the compound-sequestering structures, the plurality of heat receiving elements comprising a material that is more heat-conductive than the substrate, the plurality of heat receiving elements being exposed on the second side,
    wherein each of the plurality of compound-sequestering structures is configured to release a compound into the air when heated to a predetermined temperature.

2. The apparatus of claim 1, wherein each of the plurality of compound-sequestering structures comprises a waxy phase and a volatile phase.

3. The apparatus of claim 2, wherein the volatile phase of at least one of the compound-sequestering structures includes at least one compound with an odor detectable by a laboratory animal.

4. The apparatus of claim 3, wherein the odor is of a potential mate or of a predator.

5. The apparatus of claim 2, wherein the plurality of compound-sequestering structures comprises:
    a first set of compound-sequestering structures, each compound-sequestering structure in the first set containing a first volatile compound; and
    a second set of compound-sequestering structures, each compound-sequestering structure in the second set containing a second volatile compound distinct from the first volatile compound.

6. The apparatus of claim 5, wherein:
    the first set of compound-sequestering structures are spatially arranged in a first column; and
    the second set of compound-sequestering structures are spatially arranged in a second column that is not collinear with the first column.

7. The apparatus of claim 2, wherein at least one of the compound-sequestering structures comprises a plurality of microvesicles that are surrounded by an encapsulant made of waxy phase.

8. The apparatus of claim 1, wherein each of the plurality of compound-sequestering structures is positioned on at least one of the plurality of heat receiving elements, and the plurality of heat receiving elements comprise metal printed on the second side of the card.

9. The apparatus of claim 1, wherein the card comprises a plurality of gaps, each gap positioned between two or more of the plurality of compound-sequestering structures.

10. The apparatus of claim 1, wherein the card includes computer-readable markings that indicate one or more types of compounds contained within the plurality of compound-sequestering structures.

11. The apparatus of claim 1, wherein the card comprises heat-insulating plastic foam between two or more of the plurality of compound-sequestering structures.

12. The apparatus of claim 1, wherein the plurality of heat receiving elements are in contact with the plurality of compound-sequestering structures.

13. The apparatus of claim 1, wherein at least one of the plurality of compound-sequestering structures comprises a layer having a thickness of from about 0.5 mm to about 2.0 mm.

14. An apparatus for releasing compounds into a living space of an experimental animal, the apparatus comprising:

a cage comprising one or more walls that enclose a living space for an experimental animal;

a card adapted to be positioned inside the cage or in an air supply pathway to the cage, the card comprising a plurality of compound-sequestering structures to release compounds into the living space of the cage;

a heating structure adapted to be positioned outside the cage, the heating structure comprising a two-dimensional array of laser or infrared sources adapted to align with the respective compound-sequestering structures and selectively direct their outputs toward the respective compound-sequestering structures; and a controller configured to independently control an intensity of emission from each of the laser or infrared sources to cause a corresponding compound-sequestering structure to release compounds into the atmosphere of the living space.

15. The apparatus of claim 14, wherein the controller is further configured to incrementally vary an intensity of radiation emitted from each of the plurality of laser or infrared sources.

16. The apparatus of claim 14, wherein each of the plurality of laser or infrared sources is an IR LED.

17. The apparatus of claim 14, wherein the laser or infrared sources are adapted to selectively direct their outputs onto heat-receiving elements that are aligned behind the compound-sequestering structures.

18. The apparatus of claim 14, wherein each of the plurality of laser or infrared sources is a laser.

19. The apparatus of claim 14, wherein:

the heating structure comprises a camera configured to capture an image of fiducial markings on the card; and the controller is configured to drive the array of laser or infrared sources based at least in part on the captured image.

20. An apparatus for sequestering and releasing compounds into the air, the apparatus comprising:

a card with a first side and a second side;

a plurality of compound-sequestering structures affixed to the first side, at least one of the plurality of compound-sequestering structures comprising (i) a first layer that comprises a first compound-sequestering waxy phase and is exposed on the first side and (ii) a second layer, under the first layer, that comprises a second compound-sequestering waxy phase that is different from the first compound-sequestering material, wherein each of the plurality of compound-sequestering structures is configured to release a compound into the air when heated to a predetermined temperature, and wherein the first layer is adapted to be selectively melted relative to the second layer and to be substantially removed through heating to expose a surface of the second layer on the first side.

* * * * *